United States Patent [19]

Shimizu et al.

[11] Patent Number: 5,097,061
[45] Date of Patent: Mar. 17, 1992

[54] METHOD FOR PREPARING ALPHA-(4-ISOBUTYLPHENYL)PROPIONIC ACID OR ITS PRECURSOR

[75] Inventors: Isoo Shimizu; Yasuo Matsumura; Yuuichi Tokumoto; Kazumichi Uchida, all of Yokohama, Japan

[73] Assignee: Nippon Petrochemicals Co., Ltd., Tokyo, Japan

[21] Appl. No.: 368,049

[22] Filed: Jun. 19, 1989

[30] Foreign Application Priority Data

Jun. 24, 1988 [JP] Japan .................. 63-156331
Jun. 24, 1988 [JP] Japan .................. 63-156332
Dec. 13, 1988 [JP] Japan .................. 63-314152
Dec. 13, 1988 [JP] Japan .................. 63-314155

[51] Int. Cl.$^5$ .......................... C07C 69/76
[52] U.S. Cl. .................. 560/105; 562/406; 562/418; 562/419; 562/496; 568/429; 585/444; 585/445; 585/452; 585/446; 585/467; 585/468; 585/458; 585/464; 585/466
[58] Field of Search .............. 562/406, 418, 419, 496; 560/105; 585/445, 452, 444, 462

[56] References Cited

U.S. PATENT DOCUMENTS

| | | | |
|---|---|---|---|
| 2,407,373 | 9/1946 | Kearby | 585/445 |
| 2,888,499 | 5/1959 | Pitzer | 585/445 |
| 2,995,610 | 8/1961 | Schaap | 585/452 |
| 3,291,847 | 12/1966 | Warner | 585/452 |
| 3,437,703 | 4/1969 | Reitmeier | 585/444 |
| 3,631,213 | 12/1971 | Brewer | 585/445 |
| 3,911,034 | 10/1975 | Sato | 585/444 |
| 4,463,207 | 7/1984 | Johnson | 585/462 |
| 4,694,100 | 9/1987 | Shimizu | 560/105 |
| 4,902,845 | 2/1990 | Kim | 585/444 |
| 4,914,250 | 4/1990 | Smith | 585/452 |

FOREIGN PATENT DOCUMENTS 0168802  1/1986  European Pat. Off. .
01688031 1/1986  European Pat. Off. .
0170147  2/1986  European Pat. Off. .

OTHER PUBLICATIONS

Olah, "Friedel-Crafts and Related Reactions," vol. II, part 1., pp. 1-37, 116-179 & 259-288 (1964.

Primary Examiner—Michael L. Shippen
Attorney, Agent, or Firm—Scully, Scott, Murphy & Presser

[57] ABSTRACT

A method for preparing α-(4-isobutylphenyl)propionic acid or its precursor is here disclosed which comprises a step A of forming p-isobutylstyrene from p-isobutylethylbenzene and a step B of forming α-(4-isobutylphenyl)propionaldehyde from p-isobutylstyrene or a step C of forming α-(4-isobutylphenyl)propionic acid or its alkyl ester from p-isobutylstyrene.

Furthermore, a method for preparing said p-isobutylethylbenzene is also disclosed which comprises alkylating isobutylbenzene or 4-ethyltoluene with ethylene or propylene.

38 Claims, 1 Drawing Sheet

METHOD FOR PREPARING ALPHA-(4-ISOBUTYLPHENYL)PROPIONIC ACID OR ITS PRECURSOR

BACKGROUND OF THE INVENTION

1. Field of the Invention

The present invention relates to a method for preparing α-(4-isobutylphenyl)propionic acid, its precursor, i.e., α-(4-isobutylphenyl)propionaldehyde, or an alkyl α-(4-isobutylphenyl)propionate at low cost and in high purity.

More specifically, the present invention relates to a method for preparing α-(4-isobutylphenyl)propionic acid or its precursor which comprises the steps of dehydrogenating p-isobutylethylbenzene to form p-isobutylstyrene, and carbonylating p-isobutylstyrene to form α-(4-isobutylphenyl)propionic acid or its precursor, i.e., α-(4-isobutylphenyl)propionaldehyde or an alkyl α-(4-isobutylphenyl)propionate.

Another method of the present invention contains the step of forming p-isobutylethylbenzene. That is, the second method of the present invention comprises the three steps of the step I of alkylating isobutylbenzene or 4-ethyltoluene with ethylene or propylene to from p-isobutylethylbenzene, the step II of dehydrogenating p-isobutylethylbenzene to form p-isobutylstyrene, and the step III of carbonylating p-isobutylstyrene to form α-(4-isobutylphenyl)propionic acid or its precursor, i.e., α-(4-isobutylphenyl)propionaldehyde or an alkyl α-(4-isobutylphenyl)propionate.

This α-(4-isobutylphenyl)propionic acid is a useful medicine (trade name Ibuprophen) having alleviation effects of fever and pain and antiphlogistic effect, as described in British Patent No. 971700, French Patent No. 1549758 and the like.

It is known that α-(4-isobutylphenyl)propionaldehyde obtained in the step III of the present invention can be easily converted into α-(4-isobutylphenyl)propionic acid by oxidization in a known manner. Similarly, the alkyl α-(4-isobutylphenyl)propionate can be easily converted into α-(4-isobutylphenyl)propionic acid by hydrolysis with an acid or an alkali in a known manner. Therefore, each of these compounds can be considered to be the precursor for the preparation of α-(4-isobutylphenyl)propionic acid.

2. Description of the Prior Art

Heretofore, α-(4-isobutylphenyl)propionic acid and its precursor have been synthesized from an extremely great number of compounds as starting materials by various methods.

However, in order to synthesize α-(4-isobutylphenyl)propionic acid and its precursor at low cost and in high purity, the following requirements are needful:

(a) Starting materials should be simple compounds.

(b) In a reaction to be utilized, an intermediate in the each step should also be as simple and stable as possible.

(c) In place of expensive reagents, inexpensive reagents or catalysts should be employed.

(d) The number of steps for the synthesis should be as few as possible.

(e) Since an isobutyl group is liable to bring about skeletal isomerization, it is necessary to use a reaction in which the isomerization and other undesirable phenomenons are inhibited as much as possible.

For example, in Japanese Patent Laid-open Publication No. 100042/1976 which suggests a synthetic method of a-(4-isobutylphenyl)propionaldehyde, a Grignard reagent of isobutylbenzene which is unstable and difficult to handle is used as the starting material, and a Lewis acid such as $BF_3$ is also used. Therefore, the isobutyl group tends to isomerize. Furthermore, in Japanese Patent Laid-open Publication No. 82740/1978, a compound such as metallic lithium which is difficult to handle is utilized.

Additionally, in Japanese Patent Laid-open Publication No. 13351/1974 which discloses a method for the preparation of α-(4-isobutylphenyl)propionic acid, isobutylbenzene is used as the starting material, but aluminum chloride is used as a catalyst. Thus, the isobutyl group tends to isomerize. In addition, expensive reagents are used.

In methods described in French Patent No. 1549758 and British Patent No. 1160725, p-isobutylacetophenone is used as the starting material.

However, p-isobutylacetophenone is not considered to be an inexpensive compound for the undermentioned reason. The most economical synthesis of p-isobutylacetophenone is to use isobutylbenzene as the starting material, but it is not preferable from an economical viewpoint to convert isobutylbenzene into p-isobutylacetophenone. That is, for the sake of the conversion into p-isobutylacetophenone, it is indispensable to make use of acetyl chloride which is an expensive and unstable material, and in addition, anhydrous aluminum chloride which is very sensitive to water must be used as a reaction catalyst at least in an amount equimolar with acetyl chloride, i.e., in a large amount. For example, even if this conversion reaction proceeds stoichiometrically in a yield of 100%, anhydrous aluminum chloride as much as 700 kg must be used to manufacture 1 ton of p-isobutylacetophenone. Moreover, after the end of the reaction, 410 kg of aluminum hydroxide and 750 kg of a chlorine ion result from the inactivation of anhydrous aluminum chloride, and thus it is additionally necessary to treat 1,160 kg of wastes, the amount of which is much greater than that of the manufactured p-isobutylacetophenone, so as to make them harmless. For this reason, p-isobutylacetophenone as the starting material is expensive, and needless to say, the process using this starting material is expensive. Furthermore, the conversion of p-isobutylacetophenone into α-(4-isobutylphenyl)propionic acid proceeds intricate intermediates, and it is fair to say that known method is not always economical from an industrial viewpoint.

U.S. Pat. No. 4,694,100 suggests a method for preparing α-(4-isobutylphenyl)propionic acid from p-isobutylstyrene through a hydroformylation reaction or a Reppe reaction. This method is economically excellent, because p-isobutylstyrene which is the starting material is simple and stable, and because the hydroformylation reaction and the Reppe reaction do not require expensive reagents. However, in these conventional manufacturing methods using p-isobutylstyrene, a complex reaction route is taken or expensive reagents are employed, so that the above-mentioned advantages are lost.

Japanese Patent Laid-open Publication No. 24534/1986 discloses a method which comprises subjecting isobutylbenzene and acetaldehyde to condensation reaction in the presence of a sulfuric acid catalyst to form 1,1-bis(p-isobutylphenyl)ethane, catalystically decomposing the latter to p-isobutylstyrene by the use of an acid catalyst, reacting the resultant compound with carbon monoxide and hydrogen in the presence of a carbonylation complex catalyst in order to obtain α-(4- isobutylphenyl)propionaldehyde. However, since the above-mentioned method employs sulfuric acid, the sulfonation reaction of isobutylbenzene itself which is the valuable raw material cannot be avoided, so that a part of isobutylbenzene is lost as a sulfonated compound, which means that the method is economically unpreferable. In addition, since this condensation reaction is a dehydration reaction, sulfuric acid which is used as the catalyst is diluted with the resulting water, and thus in order to reuse the catalyst, the diluted sulfuric acid must be treated by, for example, high-temperature distillation, in which devices are liable to corrode. Additionally, a great deal of the sulfonated compound is dissolved in a sulfonic acid phase, and therefore the catalyst concentration cannot be easily recovered by the simple distillation. In consequence, the resultant water must be removed through chemical reaction by the use of anhydrous sulfuric acid or fuming sulfuric acid, with the result that the cost of the catalyst increases.

As discussed above, the conventional techniques regarding the manufacture of α-(4-isobutylphenyl)propionaldehyde are not considered to be economical, and the development of more convenient manufacturing methods is demanded.

SUMMARY OF THE INVENTION

An object of the present invention is to provide a method for preparing α-(4-isobutylphenyl)propionic acid, which is a useful medicine, from a known compound, i.e., p-isobutylethylbenzene at low cost and in high purity. In this case, p-isobutylethylbenzene can be prepared from fundamental chemicals such as isobutylbenzene or 4-ethyltoluene economically and in a high-purity state.

Another object of the present invention is to provide a method for preparing p-isobutylethylbenzene by disproportionating o-isobutylethylbenzene or m-isobutylethylbenzene which are novel substances. The other objects of the present invention will be apparent from the undermentioned description.

The first feature of the present invention relates to a method for preparing α-(4-isobutylphenyl)propionic acid or its precursor which comprises the following steps A and B or C:

The Step A

The formation of p-isobutylstyrene by dehydrogenating p-isobutylethylbenzene in a gaseous phase in the presence of a dehydrogenation metallic catalyst containing at least one metal selected from the group consisting of elements in the groups IB, IIB, VIA, VIIA and VIII of the periodic table under conditions of a reaction temperature of 300° to 650° C., a reaction pressure of 50 kg/cm² or less, a contact time of 0.005 to 20 seconds and a p-isobutylethylbenzene conversion of 80% by weight or less;

The Step B

The formation of α-(4-isobutylphenyl)propionaldehyde by reacting p-isobutylstyrene obtained in the step A with carbon monoxide and hydrogen at a reaction temperature of 40° to 150° C. under a carbon monoxide partial pressure of 10 kg/cm² or more in the presence of a transition metal complex carboxylation catalyst; and The Step C The formation of desired α-(4-isobutylphenyl)propionic acid or its alkyl ester by reacting p-isobutylstyrene obtained in the step A with carbon monoxide and water or a lower alcohol at a reaction temperature of 40° to 250° C. under a carbon monoxide partial pressure of 10 kg/cm² or more in the presence of a transition metal complex carbonylation catalyst.

The second feature of the present invention relates to an industrial and economical method for preparing α-(4-isobutylphenyl)propionic acid or its precursor which comprises the steps of a step I of forming p-isobutylethylbenzene which is a step IA or a step IB of alkylating isobutylbenzene or 4-ethyltoluene with ethylene or propylene; a step II of forming p-isobutylstyrene by dehydrogenating p-isobutylethylbenzene; and a step III of forming α-(4-isobutylphenyl)propionic acid or its precursor which is a step IIIA or a step IIIB of carbonylating p-isobutylstyrene:

The Step I: The Following Step IA or IB

The step IA: the formation of p-isobutylethylbenzene by reacting isobutylbenzene with ethylene at a reaction temperature of −10° to 600° C. in a molar ratio of ethylene/isobutylbenzene=0.005–100 under a reaction pressure of 1 kg/cm² or more in the presence of an acid catalyst;

The step IB: the formation of a fraction of containing 4-isobutylethylbenzene and having a boiling point in the range of 190° to 220° C. or less (in terms of atmospheric pressure) by reacting 4-ethyltolunene with propylene at a temperature of 150° to 250° C. under a pressure of 15 kg/cm² or more in the presence of 3 milligram atom or more of an alkali metal with respect to 1 mole of 4-ethyltolunene;

The Step II

The formation of p-isobutylstyrene by dehydrogenating p-isobutylethylbenzene in a gaseous phase under conditions of a reaction temperature of 300° to 650° C., a reaction pressure of 50 kg/cm² or less, a contact time of 0.005 to 20 seconds and p-isobutyethylbenzene conversion of 80% by weight or less in the presence of a dehydrogenation metallic catalyst containing a metal selected from the group consisting of elements in the groups IB, IIB, VIA, VIIA and VIII of the periodic table;

The Step III: The Following Step IIIA or Step IIIB:

The Step IIIA: the formation of α-(4-isobutylphenyl)-propionaldehyde by reacting p-isobutylstyrene with carbon monoxide and hydrogen in the presence of a transition metal complex carbonylation catalyst under conditions of a reaction temperature of 40° to 150° C. and a mixed pressure of carbon monoxide and hydrogen of 10 to 600 kg/cm²;

The Step IIIB: the formation of desired α-(4-isobutylphenyl)propionic acid or its alkyl ester by reacting p-isobutylstyrene with carbon monoxide and water or an alcohol in the presence of a transition metal complex carbonylation catalyst under conditions of a reaction temperature of 40° to 250° C. and a carbon monoxide partial pressure of 10 to 600 kg/cm².

DETAILED DESCRIPTION OF THE INVENTION

Figure 1:
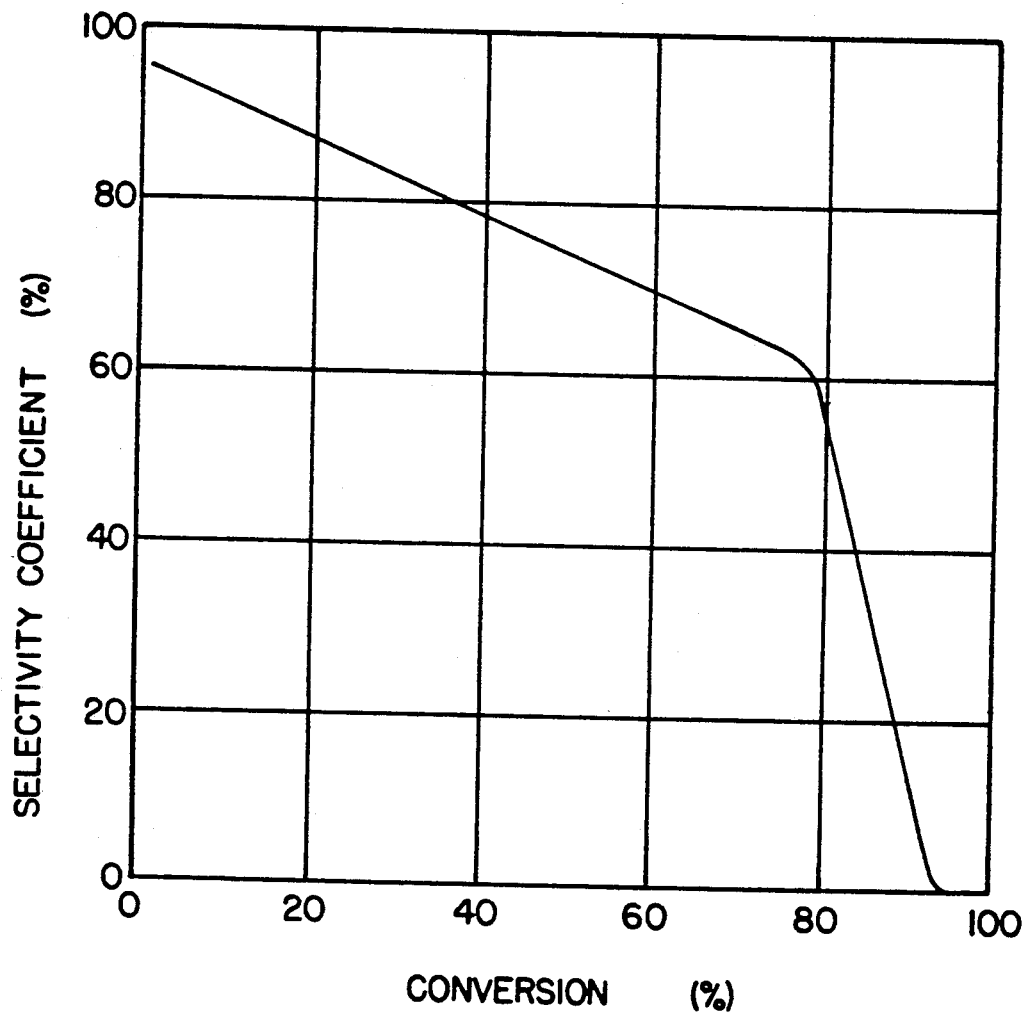
FIG. 1 shows a relation between the conversion of p-isobutylethylbenzene and the selectivity coefficient of p-isobutylstyrene in dehydrogenation reaction. Solid lines in FIG. 1 are concerned with Experimental Examples 24 to 33 of the present invention.

The inventors of the present application notice the dehydrogenation of p-isobutylethylbenzene as a means for preparing p-isobutylstyrene at low cost. Furthermore, they also take up the ethylation of isobutylbenzene with ethylene as a means for preparing p-isobutylethylbenzene economically. Not only the combination of these means but also each single reaction thereof has not been known at all. In addition, it can be presumed from the conventional techniques that the combination of such simple reactions is very difficult.

The ethylation reaction of a monoalkylbenzene with ethylene in the presence of an acid catalyst is well known. For example, according to a method described in Kuts, W. M. & B. B. Corson, J. Org. Chem., 16, p. 699 (1951), ethyltoluene can be produced in a ratio of o:m:p=29:50:21 by reacting toluene with ethylene in the presence of a silica-alumina catalyst. In this connection, the present inventors have further investigated, and they have found that when ethylene is reacted with ethylbenzene in the presence of the silica-alumina catalyst, diethylbenzene is produced in a ratio of o:m:p=28:31:41; when ethylene is reacted with isopropylbenzene, isopropylethylbenzene is produced in a ratio of o:m:p=24:39:37; and when ethylene is reacted with sec-butylbenzene, sec-butylethylbenzene is produced in a ratio of o:m:p=12:49:39. Allen, R. H. & L. D. Yats, J. Am. Chem. Soc., 83, p. 2799 (1961) describes that when toluene is reacted with ethylene in the presence of a hydrogen fluoride catalyst, ethyltoluene is produced in a ratio of o:m:p=42:33:25, and it has been confirmed that this ratio is an equilibrium composition. Furthermore, Schlatter, M. J. & R. D. Clark, J. Am. Chem. Soc., 75, p. 361 (1953) describes that when toluene is reacted with isobutene in the presence of hydrogen fluoride, tert-butyltoluene is produced in a ratio of m:p=67-7:33-93 and the production of o-tert-butyltoluene is not observed. However, when toluene is alkylated with 1-butene or 2-butene, sec-butyltoluene is produced in a ratio of o:m:p=35:33:32. It has been also confirmed that even when toluene is alkylated with propylene, the ratio of o:m:p is 41:26:33.

As described above, in order to investigate the orientation of the position isomerism of a product which is obtained by alkylating a monoalkylbenzene, there is no means but the way of researching compounds one by one. Most of the reaction products obtained by the above-mentioned methods are mixtures of o-, m- and p-position isomers. As well known, however, it is usually difficult to separate the three kinds of position isomers of the dialkylbenzene in high purity by distillation. For example, boiling points of o-, m- and p-isomers of xylene are 144.4° C., 139.1° C. and 138.4° C. (in terms of atmospheric pressure), respectively, and the boiling points of o-, m- and p-isomers of ethyltoluene are 165.2° C., 161.3° C. and 162.0° C., respectively. The o-isomer can be separated from the position isomer mixture by the distillation, though it is not easy. However, the separation of the m- and p-isomers from each other by the distillation is very difficult. The boiling points of o-, m- and p-isomers of isopropyltoluene are 178° C., 175° C. and 177° C., respectively; the boiling points of o-, m- and p-isomers of diethylbenzene are 183° C., 182° C. and 184° C., respectively; and the boiling points of o,, m- and p-isomers of sec-butyltoluene are 196° C., 194° C. and 197° C., respectively. In these cases, it is very hard to separate and purify any isomer in high purity from each position isomer mixture by the distillation. In addition, the boiling points of o-, m- and p-isomers of isopropylethylbenzene are 193° C., 192° C. and 197° C., respectively, and the p-isomer can be separated from the position isomer mixture by the distillation, though it is not easy. However, the separation of the o- and m-isomers from each other by the distillation is very difficult.

The product, which the ethylation process of the present invention aims, is p-isobutylethylbenzene, but the method for the alkylation of isobutylbenzene with ethylene has not been reported. Therefore, there are not known a ratio of position isomers of isobutylethylbenzene in a reaction mixture and a method for separating high-purity p-isobutylethylbenzene from the mixture. Needless to say, it is not known at all, either, that p-isobutylethylbenzene can be used as the raw material of α-(4-isobutylphenyl)propionic acid.

Furthermore, a method for preparing p-isobutylethylbenzene by alkylating a side chain of 4-ethytoluene is not known, either.

With regard to the dehydrogenation reaction of aromatic hydrocarbons, some conventional techniques are present, but there is not known a technique of selectively dehydrogenating a specific substituent alone in a polyalkylbenzene containing alkyl groups which have different structures and which might be arbitrarily dehydrogenated. For example, U.S. Pat. No. 4,417,084 discloses methods for preparing methylstyrene by dehydrogenating methylethylbenzene; U.S. Pat. No. 4,393,268 discloses methods for preparing tert-butylstyrene by dehydrogenating tert-butylethylbenzene; and European Patent Laid-open Publication No. 217492 discloses a method for preparing ethylstyrene or divinylbenzene by dehydrogenating diethylbenzene. However, methylethylbenzene and tert-butylethylbenzene both have an ethyl group, which might be dehydrogenated, and other substituents of a methyl group and a tert-butyl group which cannot be dehydrogenated. Therefore, a secondary reaction in the dehydrogenation of these compounds is a cracking reaction, and the selectivity of the dehydrogenation reaction itself is not disturbed. Furthermore, when diethylbenzene having two alkyl groups, i.e., two ethyl groups which might be dehydrogenated is dehydrogenated, either of the ethyl groups is dehydrogenated to form ethystyrene alone. Therefore, it is unnecessary to select either of the two substituents, and since the aimed product is divinylbenzene, the remaining ethyl group of the ethylstyrene is afterward dehyrogenated conveniently. To sum up, the two ethyl groups are not differential, and the dehydrogenation can proceed without any problem.

The technique of the present invention of preparing p-isobutylstyrene by the selective dehydrogenation of p-isobutylethylbenzene is basically different from these known techniques. In the concrete, the substituents bonded to the aromatic ring of p-isobutylethylbenzene which is the raw material are an ethyl group and an isobutyl group, and these groups can be converted into a vinyl group and a 2-methyl-1-propenyl group or a 2-methyl-2-propenyl group (hereinafter referred to as "substituted propenyl group" sometimes) by the dehydrogenation. That is, when the ethyl group alone of p-isobutylethylbenzene is dehyrogenated, p-isobutylstyrene is formed, and when the isobutyl group alone is dehydrogenated, 4-(2'-methyl-1'-propenyl)ethylbenzene or 4-(2'-methyl-2'-propenyl)ethylbenzene is formed. Furthermore, when both of the ethyl group and the isobutyl group are dehydrogenated, 4-(2'-methyl-1'-propenyl)vinylbenzene or 4-(2'-methyl-2'-propenyl)vinylbenzene is formed. As is apparent from the foregoing, p-isobutylethylbenzene has the two different alkyl groups which can be dehydrogenated, and a product largely depends upon the group to be dehydrogenated.

In Journal of Catalysis 34, p. 167-174 (1974), it is reported that a dehydrogenation reaction rate constant of cumene is twice as much as that of ethylbenzene in the case that a $Bi_2UO_6$-uraminum oxide catalyst is used. Moreover, in Azerb. Khim. Zh., (2), p. 59-62 (Russ), 1968, it is reported that with regard to the dehydrogenation selectivity of the alkyl group in one molecule of isopropylethylbenzene by the dehydrogenation, a ratio of the production of isopropenylethylbenzene in which an isopropyl group alone is dehydrogenated to that of isopropylstyrene in which an ethyl group alone is dehydrogenated is 2 or more, and when reaction temperature is lowered to heighten the selectivity coefficient, the above-mentioned ratio becomes 3 or more. These known literatures indicate that the branched isopropyl group is dehydrogenated about twice to thrice more easily than the straight-chain ethyl group. According to the investigation of the present inventors, it has been found that when p-sec-butylbenzene is dehydrogenated in the presence of an iron oxide catalyst under conditions that a reaction temperature is 550° C., a molar ratio of steam to p-sec-butylethylbenzene is 93, and a contact time with p-sec-butylethylbenzene is 0.2 second, the conversion of p-sec-butylethylbenzene is 43.4% by weight, and the ratio of p-sec-butenylethylbenzene:p-sec-butylstyrene is about 2:1. Thus, it has been confirmed that the sec-butyl group is about twice more easily dehydrogenated than the ethyl group, and that even when the reaction conditions and the like are altered, this tendency is retained. From this fact, it can be presumed that the branched sec-butyl group having 4 carbon atoms is more easily dehydrogenated than the straight-chain ethyl group, as described in the above-mentioned literature regarding isopropylethylbenzene. However, the object of the present invention cannot be achieved by such a conception.

The product which is intended by the dehydrogenation of p-isobutylethylbenzene is p-isobutylstyrene in which the ethyl group alone is dehydrogenated. Therefore, there is strongly demanded a dehydrogenation method of p-isobutylethylbenzene in which the selectivity coefficient of p-isobutylstyrene is high, i.e., a method for selectively dehydrogenating the ethyl group alone of the ethyl and isobutyl groups which p-isobutylethylbenzene has.

In the present invention, p-isobutylethylbenzene which is manufactured by any method can be used.

p-Isobutylethylbenzene can be obtained by the following alkylation in addition to conventional known methods, and thus reference will be first made to the method of p-isobutylethylbenzene by the alkylation.

A step I of the present invention is a step of forming p-isobutylethylbenzene and comprises a step IA of forming p-isobutylethylbenzene by ethylating isobutylbenzene with ethylene or a step IB of forming p-isobutylethylbenzene by alkylating a side chain of 4-ethyltoluene with propylene. First, the above-mentioned ethylation step will be described.

Ethylation

In the ethylation step, an acid catalyst is used. Examples of the acid catalyst include usual ethylation catalysts such as solid acids, inorganic acids, organic acids, Friedel-Crafts catalysts, heteropoly acids, isopoly acids and strong acid type cation exchange resins, in the case that conditions under which an isobutyl group scarcely isomerizes are employed. Typical examples of the acid catalyst include inorganic acids such as sulfuric acid and phosphoric acid; Friedel-Crafts catalysts such as aluminum chloride, zirconium chloride, zinc chloride, vanadium chloride, titanium chloride, beryllium chloride, boron fluoride and hydrogen fluoride; organic acids such as benzenesulfonic acid, p-toluenesulfonic acid and trifluoromethanesulfonic acid; heteropoly acids; isopoly acids; solid acids such as silica-alumina and zeolite; and strong acid type cation exchange resins such as perfluorosulfonic acid resin typified by NAFION resin (trade name; made by Du Pont).

A reaction temperature is usually in the range of −10° to 600° C. When the reaction temperature is less than this range, a reaction rate is low, and the prolonged reaction time is necessary to heighten the conversion of the ethylation inconveniently. Inversely, when the reaction temperature is in excess of this range, the decomposition reaction or the structure isomerization of the isobutyl group occurs noticeably, so that produced p-isobutylethylbenzene is further ethylated as a secondary reaction unpreferably.

Here, the preferable etylation catalyst will be described in detail.

In the case that silica-alumina is used as the catalyst, this silica-alumina may be natural or synthetic one, or a mixture thereof. In this case, the reaction temperature is preferably from 150° to 600° C., more preferably from 200° to 500° C. In the case that trifluoromethanesulfonic acid and/or hydrogen fluoride is used as the catalyst, trifluoromethanesulfonic acid or hydrogen fluoride may be used in the form of a pure product, an aqueous solution or a mixture thereof. As a result of the researches of the present inventors, it has been found that trifluoromethanesulfonic acid and hydrogen fluoride have about the same catalytic effect in the ethylation of isobutylbenzene, and they provide about the same products under the same conditions. In this case, the reaction temperature is preferably from −10° to 200° C., more preferably from −5° to 150° C.

In the case that the heteropoly acid is used as the catalyst, examples of the usable heteropoly acid include various heteropoly acids of tungsten and molybdenum of such as silicotungstic acid, phosphotungstic acid, silicomolybdic acid and phosphomolybdic acid. Furthermore, usable examples of the hetero-atom include P, B, V, As, Si, Ge, Sn, Ti, Zr, Ce, Th, Fe, Pt, Mn, Co, Ni, Te, I, Al, Cr, Rh, Cu and Se. In this case, the reaction temperature is preferably from 150° to 600° C., more preferably from 200° to 500° C.

When a strong acid type cation exchange resin such as NAFION resin is used, the reaction temperature is from 50° to 300° C., preferably 100° to 250° C.

In the case that zeolite is used as the catalyst, examples of the usable zeolite include hydrogen zeolites such as HX type zeolites, HY type zeolites and hydrogen faujasite. These hydrogen zeolites show strong solid acidity and are made by subjecting, to cation exchange, an alkali metal salt of a zeolite such as an NaX zeolite, an NaY zeolite or an Na faujasite so as to convert a part or all of the salt into proton type. In this case, the reaction temperature is preferably from 100° to 400° C., more preferably from 150° to 350° C.

The reaction pressure of ethylene is preferably 1 kg/cm² or more. When the reaction pressure is less than this level, a reaction rate is low, and the prolonged reaction time is necessary to heighten the conversion of the ethylation, which is not practical. From the viewpoint of the pressure resistance of a reactor, the practical upper limit of the reaction pressure is 100 kg/cm² or less.

The molar ratio of ethylene/isobutylbenzene which is fed to the reactor is in the range of 0.005 to 100, preferably 0.01 to 50. When the amount of ethylene is less than this ratio, the production of intended isobutylethylbenzene is insufficient, and inversely when the feed of ethylene is more than the above-mentioned ratio, by-products of di- or more-ethyl compounds such as isobutyldiethylbenzene increase disadvantageously.

The reaction phase of the ethylation may be a gaseous or a liquid phase, and the reaction system of the ethylation may be a batch system or a flow system such as a fixed bed, a moving bed or a fluidized bed. Furthermore, the introduction of ethylene into the reactor can be carried out by a closed system or a stream system.

In the ethylation, a suitable solvent can be used, so long as it is inactive in the ethylation reaction and is easily separated from the aimed product.

In the reaction product under the above-mentioned conditions, isobutylethylbenzene is present in the form of a mixture of o-, m- and p-isomers of isobutylethylbenzene.

The three isobutylethylbenzene position isomers in the ethylation reaction mixture obtained by such a procedure as described above do not have any significant difference of reactivity thereamong in a dehydrogenation reaction of the next step and a carbonylation reaction such as a hydroformylation of the further subsequent step. That is, the three isomers are scarcely separated by utilizing the difference in reactivity in the downstream steps. Therefore, it is necessary that p-isobutylethylbenzene which is used as the raw material in the next dehydrogenation step is separated in high purity in this step.

The present inventors have found that p-isobutylethylbenzene can be separated in high purity by distillation, if specific conditions are used.

That is, a feed flow into a distillation column should be the mixture containing the position isomers of isobutylethylbenzene, and the weight ratio of the p-isomer to the total of the position isomers of isobutylethylbenzene should be 5% or more, preferably 10% or more. When isobutylbenzene is ethyhlated, the content of p-isobutylethylbenzene in the position isomer mixture is usually at most 60% or so. The content of p-isobutylethylbenzene depends upon the preparation manner of isobutylethylbenzene and the reaction conditions to some extent. In short, it is preferable to use isobutylethylbenzenes in which the content of the p-isomer is high.

Components other than isobutylethylbenzenes may be contained in the mixture, and these components are not limited, so long as they do not hinder the achievement of the object of the present invention. Examples of the components other than isobutylethylbenzenes in the mixture inlcude benzene, toluene, xylene, ethylbenzene, isopropylbenzene, n-propylbenzene, sec-butylbenzene, n-butylbenzene, tert-butylbenzene, isobutylbenzene, diethylisobutylbenzene, triethylisobutylbenzene, acetone, methyl ethyl ketone, diethyl ketone, diethyl ether, hexane, heptane and octane. When the weight ratio of the p-isomer to the total of the position isomer mixture is less than 5%, the content of the aimed component in the mixture is too low, and even if highly accurate distillation is performed, high-purity p-isobutylethylbenzene cannot be separated effectively.

Furthermore, in the distillation column used in the present invention, the number of theoretical plates is 20 or more, preferably 30 or more. When the number of the theoretical plates is less than 20, high-purity p-isobutylethylbenzene cannot be separated effectively by distillation.

In the present invention, p-isobutylethylbenzene is recovered as a fraction mainly comprising components in a boiling point range of 213° to 216° C. (in terms of atmospheric pressure).

A distillation process is not particularly limited, and a continuous system or a batch system, reduced pressure, atmospheric pressue or applied pressure, and a single-column system or a multi-column system can be optionally chosen.

The reaction mixture obtained by the above-mentioned etylation usually contains, in addition to p-isobutylethylbenzene, a large amount of m- and o-isobutylethylbenzenes as well as isobutylpolyethylbenzenes such as isobutyldiethylbenzene and isobutyltriethylbenzene. Therefore, when p-isobutylethylbenzene is separated by the above-mentioned distillation, a large amount of m- and o-isobutylethylbenzenes as well as isobutylpolyethylbenzenes such as isobutyldiethylbenzene and isobutyltriethylbenzene are left. The present inventors have also found techniques of effectively utilizing a great deal of these isomers.

That is, one method of these techniques comprises returning at least a part of m- and o-isobutylethylbenzenes and the isobutylpolyethylbenzenes, which are left after the distillation, to the ethylation step in place of at least a part of the raw material ethylene in order to use the isomers cicularly.

According to this method, the feed of the raw material ethylene can be decreased, the selectivity coefficient of isobutylbenzene can be improved, and the by-products can be utilized effectively. The amounts of m- and o-isobutylethylbenzenes and the isobutylpolyethylbenzenes which are returned to the ethylation step IA are suitably decided, taking the reaction rate of the ethylation step IA and the like into consideration. In compliance with the amounts of m- and o-isobutylethylbenzenes and the isobutylpolyethylbenzenes which are returned to the step IA, the amount of ethylene to be fed to the step IA can be decreased suitably.

Another method of effectively utilizing the isomers formed as the by-products comprises disproportionating m- and o-isobutylethylbenzenes and the isobutylpolyethylbenzenes with the aid of a disproportionation catalyst so as to form p-isobutylethylbenzene.

Here, o- and m-isobutylethylbenzenes are represented by the following formulae (I) and (II), respectively, and they are novel compounds which have not been referred to in any literature. In addition, their effective uses have not been found heretofore.

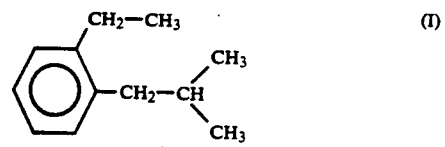
(I)

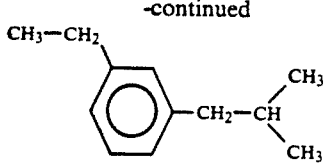

(II)

However, according to the method of the present invention, the position isomers of p-isobutylethylbenzene can be also used effectively.

That is, the present inventors have found that when m- and o-isobutylethylbenzenes, isobutylpolyethylbenzenes or a mixture thereof is disproportionated by the use of an acid catalyst, p-isobutylethylbenzene is produced.

As the catalyst for the disproportionation reaction and reaction conditions, there are utilized the acid catalyst and reaction conditions which can be used for the ethylation reaction with ethylene in the above-mentioned ethylation step. That is, examples of the usable acid catalyst for the disproportionation reaction include solid acids, inorganic acids, organic acids, Friedel-Crafts catalysts, heteropoly acids, isopoly acids and strong acid type cation exchange resins.

Typical examples of the acid catalyst include inorganic acids such as sulfuric acid and phosphoric acid; Friedel-Crafts catalysts such as aluminum chloride, zirconium chloride, zinc chloride, vanadium chloride, titanium chloride, beryllium chloride, boron fluoride and hydrogen fluoride; organic acids such as benzenesulfonic acid, p-toluenesulfonic acid and trifluoromethanesulfonic acid; heteropoly acids such as silicotungstic acid and silicomolybdic acid; isopoly acids; solid acids such as silica-alumina and zeolite; and strong acid type cation exchange resins such as perfluorosulfonic acid resin typified by NAFION resin (trade name; made by Du Pont).

The reaction temperature for the disproportionation should be suitably selected so as to inhibit secondary reactions such as decomposition reaction and the isomerization reaction of an isobutyl group as much as possible. Usually, the reaction temperature can be chosen from the range of −10° to 600° C.

Now, preferable several catalysts for the disproportionation will be described in detail.

In the case that silica-alumina is used as the catalyst, the reaction temperature is preferably from 150° to 600° C., more preferably from 200° to 500° C. When the reaction temperature is lower than the above-mentioned range, a reaction rate is low, and a prolonged reaction time is inconveniently necessary to heighten the conversion of the disproportionation. Inversely when it is higher than the above-mentioned range, the decomposition reaction and the skeletal isomerization of the isobutyl group are unpreferably noticeable.

In the case that trifluoromethanesulfonic acid and/or hydrogen fluoride is used as the catalyst, the reaction temperature is preferably from −10° to 200° C., more preferably from −5° to 150° C.

In the case that the heteropoly acid is used as the catalyst, the reaction temperature is preferably from 150° to 600° C., more preferably from 200° to 500° C.

In the case that a strong acid type cation exchange resin such as NAFION resin is used, the reaction temperature is from 50° to 300° C., preferably 100° to 250° C.

In the case that a catalytic material containing hydrogen zeolite such as HX type zeolite, HY type zeolite or hydrogen faujasite is used as the catalyst, the reaction temperature is preferably from 100° to 400° C., more preferably 150° to 350° C.

The isomer which is subjected to the disproportionation is the m- or o-isomer, the isobutylpolyethylbenzenes, or a mixture thereof. If necessary, isobutylbenzene is used together in the disproportionation reaction, and the amount of isobutylbenzene is suitably decided.

In addition, a suitable solvent can be also used in the disproportionation reaction, and any solvent can be used, so long as it does not have a bad influence on the disproportionation and the separation of p-isobutylethylbenzene.

The reaction phase of the disproportionation may be a gaseous or a liquid phase, and the reaction system of the disproportionation may be a batch system, a continuous system, for example, a fixed bed, a moving bed or a fluidized bed.

Usually, the reaction mixture obtained by the disproportionation of the present invention is a position isomer mixture of isobutylethylbenzene containing the p-isomer, and it additionally contains the isobutylpolyethylbenzenes as the by-products. Therefore, it is necessary that the p-isomer, i.e., p-isobutylethylbenzene is separated from the reaction mixture by the same method of the distillation in the above-mentioned ethylation. That is, the isobutylethylbenzene isomer mixture containing at least 5% by weight, preferably 10% by weight of p-isobutylethylbenzene is subjected to the distillation by the use of a distillation column in which the number of theoretical plates is 20 or more, preferably 30 or more in order to obtain a fraction which mainly contains components having a boiling point of 213° to 216° C. (in terms of atmospheric pressure).

p-Isobutylethylbenzene prepared by the disproportionation reaction can be fed to the subsequent step II singly or together with the p-isomer obtained in the above-mentioned ethylation step.

Alkylation of Side Chain

In the present invention, another method p-isobutylethylbenzene comprises alkylating the side chain of 4-ethyltoluene with propylene.

4-Ethyltoluene which is a starting material used in this side chain alkylation step can be prepared by any known process. One preferable example of the raw material which can be employed on an industrial scale is 4-ethyltoluene which is now produced for the purpose of manufacturing paramethylstyrene.

The side chain alkylation step is a step of reacting 4-ethyltoluene with propylene in the presence of an alkali metal catalyst to selectively alkylate, with propylene, a methyl group which is the side chain of 4-ethyltoluene.

The catalyst for the alkylation is an alkali metal in the group I of the periodic table, and sodium metal and potassium metal are preferable from an economical viewpoint. These alkali metals may be used singly in the form of a simple substance or in combination, or alternatively sodium metal, when used, may be mixed with an inorganic compound of potassium. This inorganic compound of potassium may contain, for example, potassium hydroxide, potassium carbonate, potassium bicarbonate or potassium aluminate. In the case that the inorganic compound of potassium to be used is solid, it is preferred that the solid compound has a fine particle size so as to retain good reactivity.

The amount of the alkali metal used in the alkylation is 5 milligram atom or more with respect to 1 gram mole of 4-ethyltoluene. When a mixture of sodium and the inorganic compound of potassium is used, the amount of the alkali metal is 3 milligram atom or more in terms of potassium with respect to 1 gram mole of 4-ethyltoluene. If the amount of the alkali metal or the inorganic compound of potassium is less than the above-mentioned lower limit, a reaction rate is noticeably low, which is practically unpreferable. With regard to the amount of the alkali metal, its upper limit is not restricted. However, there is the problem that a waste containing the alkali in a high proportion which is separated after the reaction must be treated subsequently. Therefore, when sodium is used, its practical upper limit is 200 milligram atom, and when the compound of potassium is used, its upper limit is 300 milligram atom in terms of potassium.

If an aromatic compound having non-aromatic double bond which conjugates with a benzene ring is added to the alkylation reaction system of the present invention, the dispersion efficiency of the catalyst is further improved, so that the reactivity is bettered. Examples of the aromatic compound having at least one non-aromatic double bond which conjugates with the benzene ring include styrene, α-methylstyrene, β-methylstyrene, vinyltoluene, divinylbenzene or indene. The amount of this aromatic compound is preferably in the range of 0.005 to 0.15 gram mole with respect to 1 gram atom of sodium. When the amount of the aromatic compound is less than 0.005 gram mole, its effect cannot be exerted, and when it is more than 0.15 gram mole, the activity of the catalyst is impaired reversely.

The reaction temperature of the alkylation is preferably in the range of 120°60 to 260° C. When the reaction temperature is less than 120° C., the reaction is slow and unpractical. The higher the reaction temperature is, the faster the reaction is, which curtails the reaction time. However, when the reaction temperature is too high, undesirable secondary reactions, for example, the generation of a sludge and decomposition occur noticeably.

With regard to the reaction pressure in the alkylation, when it is 5 kg/cm$^2$ or more, the reaction proceeds. WHen it is less than this pressure level, the reaction is too slow and unpractical. Furthermore, the upper limit of the reaction pressure is not particularly limited, and the higher the reaction pressure is, the faster the reaction is. However, if the pressure is high, a reactor must have sufficient resistance to the high pressure, and therefore the upper limit of the reaction pressure can be set to about 150 kg/cm$^2$.

After the completion of the above-mentioned side chain alkylation, p-isobutyethylbenzene is separated and recovered from the reaction mixture by means of a suitable separation manner, for example, distillation.

Dehydrogenation Step

In the dehydrogenation step II in the method of the present invention, p-isobutylethylbenzene obtained in the above-mentioned ethylation step, disproportionation step or side chain alkylation step is dehydrogenated to prepare p-isobutylstyrene. More specifically, in the dehydrogenation step II, an ethyl group alone of p-isobutylethylbenzene is selectively dehydrogenated in the presence of a dehydrogenation metal catalyst under specific conditions in order to prepare p-isobutylstyrene.

The dehydrogenation catalyst is a metallic catalyst containing a metal selected from the groups IB, IIB, VIA, VIIA and VIII of the periodic table. Typical examples of the catalyst include metallic compounds of iron, copper, zinc, nickel, palladium, platinum, cobalt, rhodium, iridium, ruthenium, chromium and molybdenum, and combinations of these compounds may be also used effectively. The preferable catalyst contains at least one metal selected from iron, copper and chromium. These metals can be used in the form of a simple substance or in the form of an oxide, a chloride, a sulfide or a hydrogen-treated compound. Furthermore, a promotor such as an alkali can be suitably used together with the catalyst. A metal-supporting catalyst can be also suitably used in which the above-mentioned metal is supported in an inorganic inactive solid carrier such as silica or pumice stone.

For the dehydrogenation reaction of the present invention, the iron oxide catalyst and the copper-chromium catalyst containing copper oxide and chrominum oxide are effective, since they have the high selectivity of p-isobutylstyrene.

Usually, the hydrogenation catalyst loses its activity gradually owing to coking and the like, while used for a long period of time. When lost, the initial activity of the catalyst can be recovered by decoking at a high temperature of, e.g., 500° C. or so with air or the like. Alternatively, the activity can be also recovered, if necessary, by putting the catalyst in a hydrogen flow at a temperature of 200° to 500° C. so as to perform a hydrogen treatment.

The reaction temperature of the dehydrogenation depends upon the composition of the catalyst, the contact time and the grade of the dilution, but it is usually from 300° to 650° C., preferably 400° to 650° C. When the reaction temperature is more than this range, secondary reactions such as decomposition reactions as well as the further dehydrogenation and decomposition of p-isobutylstyrene occur vigorously, so that the selectivity coefficient of p-isobutylstyrene deteriorates noticeably. In consequence, a great deal of p-isobutylethylbenzene is lost, and the distribution of the products is complicated fairly, with the result that it is difficult to separate p-isobutylstyrene and p-isobutylethylbenzene by the distillation or the like. When the reaction temperature is less than the above-mentioned range, a reaction rate lowers perceptibly, which is not economical, though the selectivity coefficient of p-isobutylstyrene is high.

Olefins formed by the dehydrogenation reaction are polymerizable, and thus if they are kept up at a high temperature in a high concentration in a reaction layer, a part of produced p-isobutylstyrene is plymerized and lost. In order to effectively avoid this undesirable phenomenon, it is effective that the concentration of an olefin gas is diluted with a non-reducing gas such as a nitrogen gas, a helium gas, an argon gas, steam or an oxygen gas. In addition, the olefin gas may be diluted with a solvent such as benzene which is hardly dehydrogenated. Furthermore, in order to maintain the catalyst activity for the dehydrogenation, steam can be fed to the reaction layer in the course of the dehydrogenation. The amount of steam is not particularly limited.

A reaction system in the dehydrogenation step II may be any of a fixed bed, a moving bed and a fluidized bed.

The reaction pressure for the dehydrogenation is not particularly limited, so long as it permits vaporizing p-isobutylstyrene produced under the above-mentioned reaction conditions. Nevertheless, the reaction pressure is usually 50 kg/cm² or less, and a level of from atmospheric pressure to 10 kg/cm² is preferable and economical.

The time of contact with the raw material p-isobutylethylbenzene is in the range of 0.005 to 20 seconds, preferably 0.01 to 10 seconds, more preferably 0.05 to 5 seconds. When the contact time is less than the above-mentioned range, reaction efficiency is inconveniently low. When it is more than the above-mentioned range, produced p-isobutylstyrene is further secondarily dehydrogenated, and the selectivity coefficient of p-isobutylstyrene lowers unpreferably. The contact time can be suitably altered in the above-mentioned range in accordance with a combination of the selected reaction system, the composition of a reaction gas, the composition of a catalyst, the reaction temperature, the preheating temperature of the raw material gas and the like.

Needless to say, the dehydrogenation step can be carried out by a continuous system or a batch system. Anyway, in the present invention, it is important that p-isobutylethylbenzene is dehydrogenated to p-isobutylstyrene efficiently.

The researches of the present inventors have elucidated that in the present invention, the influence of the reaction conditions and factors on the reaction can be represented by the conversion of p-isobutylethylbenzene and the selectivity coefficient of p-isobutylstyrene.

That is, the relation between the optional conversion x of p-isobutylethylbenzene obtained under the above-mentioned reaction conditions and the selectivity coefficient y of p-isobutylstyrene can be represented by the linear function $$y = ax + b$$

wherein a and b are inherent constants of the catalyst.

FIG. 1 shows the relation between the conversion of p-isobutylethylbenzene and the selectivity coefficient of p-isobutylstyrene obtained in the undermentioned examples (hereinafter referred to as "dehydrogenation performance straight line"). For example, if certain factors of the reaction conditions are set, a point on the dehyrogenation performance straight line corresponding to a certain conversion indicates the selectivity coefficient of p-isobutylstyrene which can be actually obtained. Therefore, the reaction conditions can be chosen so as to obtain the conversion of p-isobutylethylbenzene corresponding to the desired selectivity coefficient in accordance with the dehydrogenation performance straight line of the used dehydrogenation catalyst. For example, in the case of the copper-chromium catalyst, it is suitable in the present invention that the conversion of p-isobutylethylbenzene is maintained at 80% by weight or less, preferably 60% by weight or less, more preferably 50% by weight. Furthermore, in the case of the iron oxide catalyst, it is suitable in the present invention that the conversion of p-isobutylethylbenzene is maintained preferably at 80% by weight or less, more preferably 70% by weight or less. If the conversion is in excess of the range, the selectivity coefficient of p-isobutylstyrene deteriorates rapidly and diverges from the dehydrogenation performance straight line, so that not only by-products but also cracked products increase unpreferably. In the case that the conversion is in the above-mentioned range, the lower the converstion is, the higher the selectivity coefficient is. However, the productivity of p-isobutylstyrene is the product of the conversion and the selectivity coefficient, and therefore the employment of the low conversion is unpreferable, because the separation and recovery operation of unreacted p-isobutylethylbenzene by the subsequent distillation is very burdensome. From an economical viewpoint, it is desirable that the conversion is maintained at a level of 5% by weight or more.

As discussed above, if p-isobutylethylbenzene is dehydrogenated in the dehydrogenation step of the present invention, the ethyl group is exclusively dehydrogenated against convetional expectation, so that it becomes possible to prepare p-isobutylstyrene in the surprisingly high selectivity coefficient.

Carbonylation

In the carbonylation step of the present invention, p-isobutylstyrene obtained in the above-mentioned dehydrogenation step is carbonylated to form α-(4-isobutylphenyl)propionic acid or its precursor. As techniques of this carbonylation, there are hydroformylation regarding a reaction with carbon monoxide and hydrogen, hydrocarboxylation regarding a reaction with carbon monoxide and water, and hydroesterification regarding a reaction with carbon monoxide and a lower alcohol.

In the first place, reference will be made to the hydroformylation in which p-isobutylstyrene is reacted with carbon monoxide and hydrogen.

In the carbonylation step of the present invention, p-isobutylstyrene obtained in the previous step is subjected to the hydroformylation with carbon monoxide and hydrogen by the use of a transition metal complex catalyst in order to be converted into α-(4-isobutylphenyl)propionaldehyde.

The transition metal complex catalyst used in the hydroformylation is a complex catalyst comprising a transition metal such as palladium, rhodium, iridium or ruthenium. These usable transition metals have oxidation numbers of from 0 to a maximum oxidation number, and each of these transition metals is used in combination with a halogen atom, a trivalent phosphorus compound, a π-allyl group, an amine, a nitrile, an oxime, an olefin or a carbonyl complex compound having carbon monoxide and hydrogen as ligands.

Typical examples of the transition metal complex catalyst include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatriene-dichloro complex, bistriphenylphosphinedicarbonyl complex, bistriphenylphosphine acetate complex, bistriphenylphosphine dinitrate complex, bistriphenylphosphine sulfate complex and tetrakistriphenylphosphine complex, and chlorocarbonylbistriphenylphosphine complex, hydridecarbonyltristriphenylphosphine complex, bischlorotetracarbonyl complex and dicarbonylacetyl acetonate complex having carbon monoxide as a part of the ligands.

The catalyst can be fed in the form of the complex to the reaction system, or alternatively the compound which will be the ligand is fed separately to the reaction system, and the complex can be formed in the reaction system. That is, in this case, an oxide, a sulfate or a chloride of the above-mentioned transition metal is fed to the reaction system simultaneously together with a compound which will be the ligand, for example, a phosphine, a nitrile, an allyl compound, an amine, an oxime or an olefin, or carbon monoxide or hydrogen.

Examples of the phosphine include triphenylphosphine, tritolylphosphine, tributylphophine, tricyclohexylphosphine and triethylphosphine; examples of the nitrile include benzonitrile, acrylonitrile, propionitrile and benzylnitrile; examples of the allyl compound include allylchloride and allylalcohol; examples of the amine include benzylamine, pyridine, piperazine and tri-n-butylamine; examples of the oxime include cyclohexyloxime, acetoxime and benzaldoxime; and examples of the olefin include 1,5-cyclooctadiene and 1,5,9-cyclododecatriene.

The amount of the complex catalyst or the compound capable of forming the complex is from 0.0001 to 0.5 mole, preferably 0.001 to 0.1 mole, with respect to 1 mole of p-isobutylstyrene. Furthermore, the amount of the compound which can be the ligand is from 0.8 to 10 moles, preferably 1 to 4 moles with respect to 1 mole of the transition metal, which can be the nucleus of the complex, such as palladium, rhodium, iridium or ruthenium.

For the purpose of accelerating the reaction, an inorganic halide such as hydrogen chloride or boron trifluoride, or an organic iodide such as methyl iodide may be added to the reaction system.

When a halide is added, the amount of the halide is from 0.1 to 30-fold moles, preferably 1 to 15-fold moles in terms of a halogen atom with regard to 1 mole of the complex catalyst or the compound capable forming the complex. When the amount of the halide is less than 0.1 mole, the effect of the added halide is not perceptible sometimes, depending upon the kind of catalyst. When it is in excess of 30-fold moles, the activity of the catalyst deteriorates reversely, and a halogen atom is added to a double bond of p-isobutylstyrene, so that the intended reaction is inhibited unpreferably.

The hydroformylation reaction is carried out at a temperature of 40° to 150° C., preferably 55° to 110° C. When the reaction temperature is less than 40° C., a reaction rate is too low to actually achieve the hydroformylation. When it is more than 150° C., secondary reactions such as polymerization and the addition of hydrogen as well as the decomposition of the complex catalyst tend to occur unpreferably.

The reaction pressure for the hydroformylation is in the range of 10 to 600 kg/cm$^2$ in terms of a mixed pressure of carbon monoxide and hydrogen. When the reaction pressure is less than 10 kg/cm$^2$, a reaction rate is too low to actually achieve the hydroformylation. The higher the pressure is, the faster the reaction proceeds, but when the pressure is too high, it is required to sufficiently heighten the pressure resistance of a reactor. Therefore, it is natural that the upper limit of the reaction pressure is present, and it is 600 kg/cm$^2$ in practice.

The reaction is allowed to proceed until a mixed gas of carbon monoxide and hydrogen is not absorbed any more, and a reaction time is usually in the range of 4 to 20 hours.

Carbon monoxide and hydrogen necessary for the reaction may be fed to the reactor in the state of a mixed gas or separately. A molar ratio between carbon monoxide and hydrogen to be fed to the reactor can be suitably selected. That is, in the hydroformylation reaction which is the step II of the present invention, carbon monoxide and hydrogen are consumed accurately in a molar ratio of 1:1. In consequence, the feed of carbon monoxide and hydrogen in a molar ratio of 1:1 is most effective, depending upon the size of the reactor and the system of the reaction.

In the hydroformylation of the present invention, a solvent which is inactive to the hydroformylation can be used for the purpose of removing reaction heat. Examples of the solvent which is inactive to the hydroformylation include polar solvents such as ethers, ketones and alcohols, and non-polar solvents such as paraffins, cycloparaffins and aromatic hydrocarbons. However, even if no solvent is used, sufficiently preferable results can be usually obtained.

After the completion of the hydroformylation reaction, the reaction product is easily separated preferably under reduced pressure into the aimed high-purity compound α-(4-isobutylphenyl)propionaldehyde and the catalyst by the distillation. The recovered complex catalyst can be reused.

α-(4-Isobutylphenyl)propionaldehyde obtained by the present invention can be oxidized in a usual manner in order to be easily converted into α-(4-isobutylphenyl)propionic acid. The oxidation can be performed by a known oxidation manner, for example, chrominum oxidation, hypochlorous acid oxidation or permanganic acid oxidation.

Next, reference will be made to the hydrocarboxylation regarding the reaction with carbon monoxide and water, and the hydroesterification regarding the reacation with carbon monoxide and a lower alcohol.

In the hydrocarboxylation, p-isobutylstyrene is reacted with carbon monoxide and water to form α-(4-isobutylphenyl)propionic acid. Furthermore, in the hydroesterification, p-isobutylstyrene is reacted with carbon monoxide and the lower alcohol to form an alkyl ester of α-(4-isobutylphenyl)propionic acid. For example, if methyl alcohol is caused to take part in the reaction, methyl α-(4-isobutylphenyl)propionate is obtained.

In the hydrocarboxylation or the hydroesterification, a transition metal complex catalyst is used, and examples of the transition metal complex catalyst include complexes of transition metals such as palladium, rhodium and iridium, and the particularly preferable catalyst is the complex of palladium. The transition metal can be used in combination with a halogen atom, a trivalent phosphorus compound or a carbonyl complex compound and carbon monoxide as a ligand. The usable transition metal e.g., palladium has a valence of 0 or 2.

Typical examples of the transition metal complex catalyst include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatriene-dichloro complex, bistriphenylphosphinedicarbonyl complex, bistriphenylphosphine acetate complex, bistriphenylphosphine dinitrate complex, bistriphenylphosphine sulfate complex and tetrakistriphenylphosphine complex, and chlorocarbonylbistriphenylphosphine complex, hydridecarbonyltristriphenylphosphine complex, bischlorotetracarbonyl complex and dicarbonylacetyl acetonate complex having carbon monoxide as a part of the ligands.

The catalyst can be fed in the form of the complex to the reaction system, or alternatively the compound which can be the ligand is fed separately to the reaction system, and the complex may be formed in the reaction system.

The amount of the complex catalyst or the compound capable of forming the complex is from 0.0001 to 0.5 mole, preferably 0.001 to 0.1 mole, with respect to 1 mole of p-isobutylstyrene. Furthermore, the amount of the compound which will be the ligand is from 0.8 to 10 moles, preferably 1 to 4 moles with respect to 1 mole of the transition metal which will be the nucleus of the complex such as palladium, rhodium or iridium.

For the purpose of accelerating the reaction, an inorganic halide such as hydrogen chloride or boron trifluoride may be added to the reaction system.

The amount of such a halide is from 0.1 to 30-fold moles, preferably 1 to 15-fold moles in terms of a halogen atom with regard to 1 mole of the complex catalyst or the compound capable of forming the complex. When the amount of the halide is less than 0.1 mole, the effect of the added halide is not perceptible sometimes, depending upon the kind of catalyst. When it is in excess of 30-fold moles, the activity of the catalyst deteriorates reversely, and a halogen atom is added to a double bond of p-isobutylstyrene, so that the intended reaction is inhibited unpreferably.

The hydrocarboxylation or hydroesterification reaction is carried out at a temperature of 40° to 250° C., preferably 70° to 120° C. When the reaction temperature is less than 40° C., a reaction rate is too low to actually achieve the reaction. When it is more than 250° C., polymerization reaction and the decomposition of the complex catalyst occur unpreferably.

The pressure of carbon monoxide is 10 kg/cm$^2$ or more. When the pressure is less than 10 kg/cm$^2$, a reaction rate is too low to actually achieve the hydrocarboxylation or hydroesterification reaction. The higher the pressure of carbon monoxide is, the faster the reaction proceeds, but when the pressure is too high, it is required to sufficiently heighten the pressure resistance of a reactor. Therefore, it is natural that the upper limit of the reaction pressure is present, and it is 600 kg/cm$^2$ in practice.

The reaction is allowed to proceed until carbon monoxide is not absorbed any more, and the reaction time is usually in the range of 4 to 20 hours.

Examples of the usable alcohol include lower alcohols having 1 to 4 carbon atoms such as methyl alcohol, ethyl alcohol, n-propyl alcohol, isopropyl alcohol, n-butyl alcohol, sec-butyl alcohol and isobutyl alcohol, and above all, methyl alcohol is preferable.

After the completion of the hydrocarboxylation or hydroesterification reaction, the resultant reaction product can be easily separated into desired high-purity α-(4-isobutylphenyl)propionic acid or its alkyl ester and the catalyst by extraction or distillation. The thus recovered complex catalyst can be reused.

The alkyl α-(4-isobutylphenyl)propionate obtained by the present invention is hydrolyzed in the presence of an acid or an alkali catalyst in a usual manner in order to be easily converted into α-(4-isobutylphenyl)propionic acid.

In the ethylation step IA of the present invention, isobutylbenzene can be ethylated to form a mixture containing three kinds of position isomers of isobutylethylbenzene, and p-isobutylethylbenzene can be separated and recovered in high purity from the mixture by distillation. Furthermore, components other than p-isobutylethylbenzene in the reaction product can be also converted into p-isobutylethylbenzene effectively by recycling or disproportionation.

That is, high-purity p-isobutylethylbenzene can be separated from the ethylated reaction mixture of isobutylbenzene by the distillation technique of the present invention, and the other components are recycled as a raw material for the ethylation step IA, whereby the selectivity coefficient of isobutylbenzene into p-isobutylethylbenzene can be heightened.

In the case of the ethylation with the aid of the acid catalyst, the selectivity coefficient of the p-isomer is relatively low, and so it has been considered that the above-mentioned technique can hardly be applied to the reaction so as to produce the p-isomer as the desired compound. However, the above-mentioned technique of the present invention has been now established, and the conventional restriction can be eliminated. In consequence, even the ethylation by the use of the acid catalyst can be achieved economically and very advantageously.

When the dehydrogenation of p-isobutylethylbenzene is carried out under the conditions of the step II of the present invention, p-isobutylstyrene can be prepared in a high selectivity coefficient. Therefore, as described above, high-purity p-isobutylstyrene and unreacted p-isobutylethylbenzene can be prepared by subjecting the dehydrogenated reaction mixture obtained by the method of the present invention to two or three simple unit operations such as the separation from a water layer, drying and distillation. Furthermore, this unreacted p-isobutylethylbenzene can be recovered and reused as the raw material for the dehydrogenation.

Now, the present invention will be described in detail in reference to examples.

Preparation of p-isobutylethylbenzene (ethylation step IA)

EXPERIMENTAL EXAMPLE 1

In a 1-liter autoclave were placed 600 ml of isobutylbenzene having 99.8% by weight purity and 26 g of a silica-alumina catalyst IS-28 (trade name; made by Shokubai Chemicals Co., Ltd.), and the temperature in the system was raised up to 250° C. while stirring. Afterward, ethylene was fed thereto, and reaction was performed for 12 hours, while the pressure in the autoclave was maintained at 20 kg/cm$^2$. After the completion of the reaction, the used catalyst was removed by filtration and the resultant reaction mixture was then analyzed by a gas chromatography. The composition of the reaction mixture is set forth in Table 1.

TABLE 1

| Isobutylbenzene | 80.1% by weight |
|---|---|
| Isobutylethylbenzene | 14.3% by weight |
| ortho- | 5.7% by weight |
| meta- | 4.4% by weight |
| para- | 4.2% by weight |
| Isobutyldiethylbenzene | 3.7% by weight |
| Others | 1.9% by weight |

As a result, the conversion of isobutylbenzene was 19.7% by weight, a ratio of moles of produced p-isobutylethylbenzene to those of consumed isobutylbenzene (hereinafter referred to as "selectivity coefficient of p-isobutylethylbenzene") was 17.6%, and position isomers of isobutylethylbenzene were present in a ratio of o:m:p=40:31:29.

EXPERIMENTAL EXAMPLE 2

In a 1-liter autoclave were placed 600 ml of isobutylbenzene having 99.8% by weight purity and 26 g of a silica-alumina catalyst N633L (trade name; made by Nikki Chemicals Co., Ltd.), and the temperature in the system was raised up to 250° C. while stirring. Afterward, ethylene was fed thereto, and reaction was performed for 12 hours, while the pressure in the autoclave was maintained at 20 kg/cm$^2$. After the completion of the reaction, the used catalyst was removed by filtration and the resultant reaction mixture was then analyzed by a gas chromatography. The composition of the reaction mixture is set forth in Table 2.

TABLE 2

| | |
|---|---|
| Isobutylbenzene | 59.9% by weight |
| Isobutylethylbenzene | 29.0% by weight |
| ortho- | 10.7% by weight |
| meta- | 9.3% by weight |
| para- | 9.0% by weight |
| Isobutyldiethylbenzene | 7.7% by weight |
| Others | 3.4% by weight |

As a result, the conversion of isobutylbenzene was 40.0% by weight, the selectivity coefficient of p-isobutylethylbenzene was 18.7%, and position isomers of isobutylethylbenzene were present in a ratio of o:m:p=37:32:31.

EXPERIMENTAL EXAMPLE 3

A silica-alumia catalyst IS-28 (trade name; made by Shokubai Chemicals Co., Ltd.) was ground so that the particle diameter of the catalyst might be in the range of 1 to 2 mm, and a stainless steel pipe having an inner diameter of 12 mm and a length of 1 m was then packed with 64 ml (32.8 g) of the thus ground catalyst. Afterward, the atmopsshere in the pipe was replaced with nitrogen.

Isobutylbenzene having 99.8% by weight purity was then caused to flow through the above-mentioned reaction pipe at a flow rate of 64 ml/hr, and ethylene was fed thereto, while the temperature of the catalyst layer was maintained at 250° C., so as to set the pressure in the pipe to 20 kg/cm$^2$. Afterward, the flow rate of ethylene was adjusted so that a molar ratio of isobutylbenzene to ethylene might be 1. After 138 hours had elapsed since the commencement of the reaction, the reaction mixture was cooled, followed by gas-liquid separation. Anaylsis was then carried out by a gas chromatography. The composition of the reaction mixture is set forth in Table 3.

TABLE 3

| | |
|---|---|
| Isobutylbenzene | 78.6% by weight |
| Isobutylethylbenzene | 15.8% by weight |
| ortho- | 6.4% by weight |
| meta- | 4.8% by weight |
| para- | 4.6% by weight |
| Isobutyldiethylbenzene | 3.4% by weight |
| Others | 2.2% by weight |

As a result, the conversion of isobutylbenzene was 21.2% by weight, the selectivity coefficient of p-isobutylethylbenzene was 17.9%, and position isomers of isobutylethylbenzene were present in a ratio of o:m:p=41:30:29.

EXPERIMENTAL EXAMPLE 4

In a 10-liter three-necked flask was placed 6 kg of the reaction mixture obtained in Experimental Example 3, and distillation was then carried out on a batch system by the use of a distillation column in which the number of theoretical plates was 35, the aforesaid distillation column being composed of a glass pipe having an inner diameter of 30 mm and a length of 1.5 m which was packed with a filler, Heli Pack No. 3 metal made by Tokyo Tokushu Kanaami Co., Ltd. In this case, a fraction of p-isobutylethylbenzene having a purity of 97% by weight or more was prepared in an amount of 204 g (recovery 73.9%).

EXPERIMENTAL EXAMPLE 5

In a 1-liter autoclave were placed 600 ml of isobutylbenzene having 99.8% by weight purity and 30 ml of trifluoromethanesulfonic acid having 99% by weight purity, and the temperature in the system was then adjusted to 0° C. while stirring. Afterward, ethylene was fed thereto, and reaction was performed for 4 hours, while the pressure in the autoclave was maintained at 10 kg/cm$^2$. After the completion of the reaction, the resultant reaction mixture was then neutralized with Ca(OH)$_2$, washed with water, and analyzed by a gas chromatography. The composition of the reaction mixture is set forth in Table 4.

TABLE 4

| | |
|---|---|
| Isobutylbenzene | 92.3% by weight |
| Isobutylethylbenzene | 7.1% by weight |
| ortho- | 3.3% by weight |
| meta- | 1.9% by weight |
| para- | 1.9% by weight |
| Isobutyldiethylbenzene | trace |
| Others | 0.6% by weight |

As a result, the conversion of isobutylbenzene was 7.5% by weight, the selectivity coefficient of p-isobutylethylbenzene was 21.0%, and position isomers of isobutylethylbenzene were present in a ratio of o:m:p=46:27:27.

EXPERIMENTAL EXAMPLE 6

In a 1-liter autoclave were placed 600 ml of isobutylbenzene having 99.8% by weight purity and 30 ml of trifluoromethanesulfonic acid having 99% by weight purity, and the temperature in the system was then adjusted to 90° C. while stirring. Afterward, ethylene was fed thereto, and reaction was performed for 3.5 hours, while the pressure in the autoclave was maintained at 20 kg/cm$^2$. After the completion of the reaction, the resultant reaction mixture was then neutralized with Ca(OH)$_2$, washed with water, and analyzed by a gas chromatography. The composition of the reaction mixture is set forth in Table 5.

TABLE 5

| | |
|---|---|
| Isobutylbenzene | 61.2% by weight |
| Isobutylethylbenzene | 26.6% by weight |
| ortho- | 11.1% by weight |
| meta- | 7.6% by weight |
| para- | 7.9% by weight |
| Isobutyldiethylbenzene | 8.0% by weight |
| Others | 4.2% by weight |

As a result, the conversion of isobutylbenzene was 38.7% by weight, the selectivity coefficient of p-isobutylethylbenzene was 16.9%, and position isomers of isobutylethylbenzene were present in a ratio of o:m:p=42:29:29.

EXPERIMENTAL EXAMPLE 7

In a 1-liter autoclave were placed 600 ml of isobutylbenzene having 99.8% by weight purity and 30 ml of trifluoromethanesulfonic acid having 99% by weight purity, and the temperature in the system was raised up to 135° C. while stirring. Afterward, ethylene was fed thereto, and reaction was performed for 1 hour, while the pressure in the autoclave was maintained at 10 kg/cm$^2$. After the completion of the reaction, the resultant reaction mixture was then neutralized with Ca(OH)$_2$, washed with water, and analyzed by a gas chromatography. The composition of the reaction mixture is set forth in Table 6.

TABLE 6

| | |
|---|---|
| Isobutylbenzene | 45.3% by weight |
| Isobutylethylbenzene | 36.2% by weight |
| ortho- | 13.5% by weight |
| meta- | 11.2% by weight |
| para- | 11.5% by weight |
| Isobutyldiethylbenzene | 11.7% by weight |
| Others | 6.8% by weight |

As a result, the conversion of isobutylbenzene was 54.6% by weight, the selectivity coefficient of p-isobutylethylbenzene was 17.5%, and position isomers of isobutylethylbenzene were present in a ratio of o:m:p=37:31:32.

EXPERIMENTAL EXAMPLE 8

In a 1-liter autoclave were placed 600 ml of isobutylbenzene having 99.8% by weight purity and 30 ml of hydrogen fluoride having 99.7% by weight purity, and the temperature in the system was then adjusted to 0° C. while stirring. Afterward, ethylene was fed thereto, and reaction was then performed for 3 hours, while the pressure in the autoclave was maintained at 20 kg/cm$^2$. After the completion of the reaction, the resultant reaction mixture was then neutralized with Ca(OH)$_2$, washed with water, and analyzed by a gas chromatography. The composition of the reaction mixture is set forth in Table 7.

TABLE 7

| | |
|---|---|
| Isobutylbenzene | 92.7% by weight |
| Isobutylethylbenzene | 6.7% by weight |
| ortho- | 2.9% by weight |
| meta- | 1.8% by weight |
| para- | 2.0% by weight |
| Isobutyldiethylbenzene | trace |
| Others | 0.6% by weight |

As a result, the conversion of isobutylbenzene was 7.1% by weight, the selectivity coefficient of p-isobutylethylbenzene was 23.3%, and position isomers of isobutylethylbenzene were present in a ratio of o:m:p=43:27:30.

EXPERIMENTAL EXAMPLE 9

In a 1-liter autoclave were placed 600 ml of isobutylbenzene having 99.8% by weight purity and 30 ml of hydrogen fluoride having 99.7% by weight purity, and the temperature in the system was adjusted to 25° C. while stirring. Afterward, ethylene was fed thereto, and reaction was performed for 12 hours, while the pressure in the autoclave was maintained at atmospheric pressure. After the completion of the reaction, the resultant reaction mixture was then neutralized with Ca(OH)$_2$, washed with water, and analyzed by a gas chromatography. The composition of the reaction mixture is set forth in Table 8.

TABLE 8

| | |
|---|---|
| Isobutylbenzene | 94.6% by weight |
| Isobutylethylbenzene | 5.2% by weight |
| ortho- | 2.5% by weight |
| meta- | 1.3% by weight |
| para- | 1.4% by weight |
| Isobutyldiethylbenzene | none |
| Others | 0.2% by weight |

As a result, the conversion of isobutylbenzene was 5.2% by weight, the selectivity coefficient of p-isobutylethylbenzene was 22.3%, and position isomers of isobutylethylbenzene were present in a ratio of o:m:p=48:25:27.

EXPERIMENTAL EXAMPLE 10

In a 10-liter three-necked flask was placed 6 kg of the reaction mixture obtained by repeating the same procedure as in Experimental Example 6, and distillation was then carried out on a batch system by the use of a distillation column in which the number of theoretical plates was 35, the aforesaid distillation column being composed of a glass pipe having an inner diameter of 30 mm and a length of 1.5 m was packed with a filler, Heli Pack No. 3 metal made by Tokyo Tokushu Kanaami Co., Ltd. In this case, a fraction of p-isobutylethylbenzene having a purity of 97% by weight or more was prepared in an amount of 382 g (recovery 80.6%).

EXPERIMENTAL EXAMPLE 11

In a 1-liter autoclave were placed 436 g of isobutylbenzene having 99.8% by weight purity and 4.46 g of phosphotungstic acid hydrate (P2O5.24WO3.nH2O) and the temperature in the system was then raised up to 250° C. while stirring. Afterward, ethylene was fed thereto, and reaction was then performed for 12 hours, while the pressure in the autoclave was maintained at 20 kg/cm$^2$. After the completion of the reaction, the used catalyst was removed by filtration and the resultant reaction mixture was then analyzed by a gas chromatography. The composition of the reaction mixture is set forth in Table 9.

TABLE 9

| | |
|---|---|
| Isobutylbenzene | 78.3% by weight |
| Isobutylethylbenzene | 17.9% by weight |
| ortho- | 7.3% by weight |
| meta- | 5.3% by weight |
| para- | 5.3% by weight |
| Isobutyldiethylbenzene | 3.3% by weight |
| Others | 0.5% by weight |

As a result, the conversion of isobutylbenzene was 21.5% by weight, the selectivity coefficient of p-isobutylethylbenzene was 20.4%, and position isomers of isobutylethylbenzene were present in a ratio of o:m:p=40:30:30.

EXPERIMENTAL EXAMPLE 12

In a 1-liter autoclave were placed 426 g of isobutylbenzene having 99.8% by weight purity and 4.52 g of silicotungstic acid hydrate (SiO$_2$.12WO$_3$.26H$_2$O), and the temperature in the system was then raised up to 250° C. while stirring. Afterward, ethylene was fed thereto, and reaction was then performed for 12 hours, while the pressure in the autoclave was maintained at 20 kg/cm$^2$. After the completion of the reaction, the used catalyst was removed by filtration and the reaction mixture was then analyzed by a gas chromatography. The composition of the reaction mixture is set forth in Table 10.

TABLE 10

| | |
|---|---|
| Isobutylbenzene | 83.8% by weight |
| Isobutylethylbenzene | 12.1% by weight |
| ortho- | 4.7% by weight |
| meta- | 3.6% by weight |
| para- | 3.8% by weight |
| Isobutyldiethylbenzene | 2.1% by weight |
| Others | 2.0% by weight |

As a result, the conversion of isobutylbenzene was 16.0% by weight, the selectivity coefficient of p-isobutylethylbenzene was 19.6%, and position isomers of isobutylethylbenzene were present in a ratio of o:m:p=39:30:31.

EXPERIMENTAL EXAMPLE 13

In a 1-liter autoclave were placed 600 ml of isobutylbenzene having 99.8% by weight purity and 6 g of phosphomolybdic acid hydrate ($P_2O_5 \cdot 24MoO_3 \cdot nH_2O$), and the temperature in the system was then raised up to 280° C. while stirring. Afterward, ethylene was fed thereto, and reaction was then performed for 12 hours, while the pressure in the autoclave was maintained at 20 kg/cm². After the completion of the reaction, the used catalyst was removed by filtration and the reaction mixture was then analyzed by a gas chromatography. The composition of the reaction mixture is set forth in Table 11.

TABLE 11

| | |
|---|---|
| Isobutylbenzene | 82.1% by weight |
| Isobutylethylbenzene | 14.4% by weight |
| ortho- | 5.5% by weight |
| meta- | 4.5% by weight |
| para- | 4.4% by weight |
| Isobutyldiethylbenzene | 2.6% by weight |
| Others | 0.9% by weight |

As a result, the conversion of isobutylbenzene was 17.7% by weight, the selectivity coefficient of p-isobutylethylbenzene was 20.6%, and position isomers of isobutylethylbenzene were present in a ratio of o:m:p=38:31:31.

EXPERIMENTAL EXAMPLE 14

In a 15-liter three-necked flask was placed 10 kg of a reaction mixture obtained by repeating reaction under the same conditions as in Experimental Example 11, and distillation was then carried out on a batch system by the use of a distillation column in which the number of theoretical plates was 35, the aforesaid distillation column being composed of a glass pipe having an inner diameter of 30 mm and a length of 1.5 m which was packed with a filler, Heli Pack No. 3 metal made by Tokyo Tokushu Kanaami Co., Ltd. In this case, a fraction of p-isobutylethylbenzene having a purity of 97% by weight or more was prepared in an amount of 451 g (recovery 85.1%).

EXPERIMENTAL EXAMPLE 14A

In a 1-liter autoclave were placed 522 g of isobutylbenzene having 99.8% by weight purity and 26.2 g of HX zeolite, and the temperature in the system was then raised up to 160° C. while stirring. Afterward, ethylene was fed thereto, and reaction was then performed for 12 hours, while the pressure in the autoclave was maintained at 20 kg/cm². After the completion of the reaction, the used catalyst was removed by filtration and the reaction mixture was then analyzed by a gas chromatography. The composition of the reaction mixture is set forth in the following table.

TABLE

| | |
|---|---|
| Isobutylbenzene | 70.3% by weight |
| Isobutylethylbenzene | 20.6% by weight |
| ortho- | 8.1% by weight |
| meta- | 5.3% by weight |
| para- | 7.5% by weight |
| Isobutyldiethylbenzene | 4.2% by weight |
| Others | 4.9% by weight |

As a result, the conversion of isobutylbenzene was 29.6% by weight, the selectivity coefficient of p-isobutylethylbenzene was 21.0%, and position isomers of isobutylethylbenzene were present in a ratio of o:m:p=39:25:36.

EXPERIMENTAL EXAMPLE 14B

In a 1-liter autoclave were placed 522 g of isobutylbenzene having 99.8% by weight purity and 26.1 g of HY zeolite, and the temperature in the system was then raised up to 170° C. while stirring. Afterward, ethylene was fed thereto, and reaction was then performed for 12 hours, while the pressure in the autoclave was maintained at 20 kg/cm². After the completion of the reaction, the used catalyst was removed by filtration and the reaction mixture was then analyzed by a gas chromatography. The composition of the reaction mixture is set forth in the following table.

TABLE

| | |
|---|---|
| Isobutylbenzene | 66.8% by weight |
| Isobutylethylbenzene | 22.0% by weight |
| ortho- | 8.7% by weight |
| meta- | 5.5% by weight |
| para- | 7.8% by weight |
| Isobutyldiethylbenzene | 4.8% by weight |
| Others | 6.4% by weight |

As a result, the conversion of isobutylbenzene was 33.1% by weight, the selectivity coefficient of p-isobutylethylbenzene was 19.6%, and position isomers of isobutylethylbenzene were present in a ratio of o:m:p=40:25:35.

EXPERIMENTAL EXAMPLE 14C

In a 1-liter autoclave were placed 522 g of isobutylbenzene having 99.8% by weight purity and 26.2 g of hydrogen faujasite, and the temperature in the system was then raised up to 200° C. while stirring. Afterward, ethylene was fed thereto, and reaction was then performed for 12 hours, while the pressure in the autoclave was maintained at 20 kg/cm². After the completion of the reaction, the used catalyst was removed by filtration and the reaction mixture was then analyzed by a gas chromatography. The composition of the reaction mixture is set forth in the following table.

TABLE

| | |
|---|---|
| Isobutylbenzene | 71.2% by weight |
| Isobutylethylbenzene | 19.7% by weight |
| ortho- | 7.9% by weight |
| meta- | 4.9% by weight |
| para- | 6.9% by weight |
| Isobutyldiethylbenzene | 4.3% by weight |
| Others | 4.8% by weight |

As a result, the conversion of isobutylbenzene was 28.7% by weight, the selectivity coefficient of p-isobutylethylbenzene was 20.0%, and position isomers of isobutylethylbenzene were present in a ratio of o:m:p=40:25:35.

EXPERIMENTAL EXAMPLE 14D

In a 10-liter three-necked flask was placed 6 kg of a reaction mixture obtained by repeating reaction under the same conditions as in Experimental Example 14B, and distillation was then carried out on a batch system by the use of a distillation column in which the number of theoretical plates was 35, the aforesaid distillation column being composed of a glass pipe having an inner diameter of 30 mm and a length of 1.5 m which was packed with a filler, Heli Pack No. 3 metal made by Tokyo Tokushu Kanaami Co., Ltd. In this case, a fraction of p-isobutylethylbenzene having a purity of 97% by weight or more was prepared in an amount of 388 g (recovery 82.9%).

EXPERIMENTAL EXAMPLE 15

The fractions other than p-isobutylethylbenzene in Experimental Example 14 were mixed, and the mixture was then analyzed by a gas chromatography. The composition of the mixture is set forth in Table 12.

TABLE 12

| Isobutylbenzene | 81.8% by weight |
|---|---|
| Isobutylethylbenzene | 14.2% by weight |
| ortho- | 7.5% by weight |
| meta- | 5.5% by weight |
| para- | 1.2% by weight |
| Isobutyldiethylbenzene | 3.4% by weight |
| Others | 0.5% by weight |

In a 1-liter autoclave were placed 500 g of the above-mentioned mixture and 25 g of a silica-alumina catalyst N633L, and the atmosphere in the system was replaced with nitrogen. Afterward, disproportionation reaction was performed at 270° C. for 24 hours under stirring, and the used catalyst was removed from the reaction mixture by filtration. The resultant organic phase was then analyzed by a gas chromatography. The composition of the organic phase is set forth in Table 13.

TABLE 13

| Isobutylbenzene | 77.6% by weight |
|---|---|
| Isobutylethylbenzene | 16.2% by weight |
| ortho- | 3.7% by weight |
| meta- | 7.2% by weight |
| para- | 5.3% by weight |
| Isobutyldiethylbenzene | 2.8% by weight |
| Others | 3.4% by weight |

The disproportionated reaction mixture was placed in a 1-liter three-necked flask, and was then distilled in the same manner as in Experimental Example 14. In this case, a fraction of p-isobutylethylbenzene having a purity of 97% by weight or more was prepared in an amount of 15 g (recovery 56.6%).

EXPERIMENTAL EXAMPLE 16

Following the same procedure as in Experimental Example 15, 500 g of the mixture of the components in Table 12 and 25 g of trifluoromethanesulfonic acid having 99% by weight purity were placed in a 1-liter autoclave, and disproportionation reaction was then carried out at 110° C. for 24 hours under stirring. The reaction mixture was then neutralized with Ca(OH)2 and washed with water, and the resultant organic phase was then analyzed by a gas chromatography. The results are set forth in Table 14.

TABLE 14

| Isobutylbenzene | 78.7% by weight |
|---|---|
| Isobutylethylbenzene | 15.1% by weight |
| ortho- | 3.1% by weight |
| meta- | 7.3% by weight |
| para- | 4.7% by weight |
| Isobutyldiethylbenzene | 2.9% by weight |
| Others | 3.3% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 16 g (recovery 68.1%).

EXPERIMENTAL EXAMPLE 17

Following the same procedure as in Experimental Example 15, 500 g of the mixture of the components in Table 12 and 25 g of hydrogen fluoride having 99.7% by weight purity were placed in a 1-liter autoclave, and disproportionation reaction was then carried out at 110° C. for 24 hours under stirring. The reaction mixture was then neutralized with Ca(OH)$_2$ and washed with water, and the resultant organic phase was then analyzed by a gas chromatography. The results are set forth in Table 15.

TABLE 15

| Isobutylbenzene | 78.5% by weight |
|---|---|
| Isobutylethylbenzene | 15.7% by weight |
| ortho- | 3.9% by weight |
| meta- | 7.2% by weight |
| para- | 4.6% by weight |
| Isobutyldiethylbenzene | 2.7% by weight |
| Others | 3.1% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 15 g (recovery 65.2%).

EXPERIMENTAL EXAMPLE 18

Following the same procedure as in Experimental Example 15, 500 g of the mixture of the components in Table 12 and 25 g of phosphotungstic acid were placed in a 1-liter autoclave, and disproportionation reaction was then carried out at 250° C. for 24 hours under stirring. Afterward, the used catalyst was removed from the reaction mixture by filtration, and the resultant organic phase was then analyzed by a gas chromatography. The results are set forth in Table 16.

TABLE 16

| Isobutylbenzene | 77.8% by weight |
|---|---|
| Isobutylethylbenzene | 15.4% by weight |
| ortho- | 2.7% by weight |
| meta- | 7.1% by weight |
| para- | 5.6% by weight |
| Isobutyldiethylbenzene | 2.9% by weight |
| Others | 3.4% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 19 g (recovery 67.9%).

EXPERIMENTAL EXAMPLE 18A

Following the same procedure as in Experimental Example 15, 500 g of the mixture of the components in Table 12 and 25 g of HX zeolite were placed in a 1-liter autoclave, and disproportionation reaction was then carried out at 170° C. for 24 hours under stirring. Afterward, the used catalyst was removed from the reaction mixture by filtration, and the resultant organic phase was then analyzed by a gas chromatography. The results are set forth in the following table.

TABLE

| | |
|---|---|
| Isobutylbenzene | 77.1% by weight |
| Isobutylethylbenzene | 18.9% by weight |
| ortho- | 0.8% by weight |
| meta- | 11.4% by weight |
| para- | 6.7% by weight |
| Isobutyldiethylbenzene | 0.6% by weight |
| Others | 3.4% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 24 g (recovery 71.6%).

EXPERIMENTAL EXAMPLE 18B

Following the same procedure as in Experimental Example 15, 500 g of the mixture of the components in Table 12 and 25 g of HY zeolite were placed in a 1-liter autoclave, and disproportionation reaction was then carried out at 180° C. for 24 hours under stirring. Afterward, the used catalyst was removed from the reaction mixture by filtration, and the resultant organic phase was then analyzed by a gas chromatography. The results are set forth in the following table.

TABLE

| | |
|---|---|
| Isobutylbenzene | 77.2% by weight |
| Isobutylethylbenzene | 19.4% by weight |
| ortho- | 0.3% by weight |
| meta- | 12.0% by weight |
| para- | 7.1% by weight |
| Isobutyldiethylbenzene | 0.2% by weight |
| Others | 3.2% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 25 g (recovery 70.4%).

EXPERIMENTAL EXAMPLE 18C

Following the same procedure as in Experimental Example 15, 500 g of the mixture of the components in Table 12 and 25 g of hydrogen faujasite were placed in a 1-liter autoclave, and disproportionation reaction was then carried out at 200° C. for 24 hours under stirring. Afterward, the used catalyst was removed from the reaction mixture by filtration, and the resultant organic phase was then analyzed by a gas chromatography. The results are set forth in the following table.

TABLE

| | |
|---|---|
| Isobutylbenzene | 76.3% by weight |
| Isobutylethylbenzene | 19.3% by weight |
| ortho- | 0.2% by weight |
| meta- | 12.1% by weight |
| para- | 7.0% by weight |
| Isobutyldiethylbenzene | 0.2% by weight |
| Others | 4.2% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 23 g (recovery 65.7%).

EXPERIMENTAL EXAMPLE 19

In a 1-liter autoclave were placed 500 g of the mixture of the components in Table 12 and 25 g of a silica-alumina catalyst N633L, and reaction was then carried out with stirring at 250° C. for 12 hours under an ethylene pressure of 20 kg/cm². Afterward, the used catalyst was removed from the reaction mixture by filtration, and the resultant organic phase was then analyzed by a gas chromatography. The results are set forth in Table 17. In consequence, the conversion of isobutylbenzene was 24.3%, and the selectivity coefficient of p-isobutylethylbenzene was 27.8%.

TABLE 17

| | |
|---|---|
| Isobutylbenzene | 61.9% by weight |
| Isobutylethylbenzene | 25.0% by weight |
| ortho- | 9.0% by weight |
| meta- | 8.1% by weight |
| para- | 7.9% by weight |
| Isobutyldiethylbenzene | 9.8% by weight |
| Others | 3.3% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 28 g (recovery 70.9%).

EXPERIMENTAL EXAMPLE 20

In a 1-liter autoclave were placed 500 g of the mixture of the components in Table 12 and 25 g of trifluoromethanesulfonic acid, and reaction was then carried out with stirring at 110° C. for 12 hours under an ethylene pressure of 20 kg/cm². Afterward, the reaction mixture was neutralized with Ca(OH)$_2$, washed with water, and the resultant organic phase was then analyzed by a gas chromatography. The results are set forth in Table 18. In consequence, the conversion of isobutylbenzene was 26.3%, and the selectivity coefficient of p-isobutylethylbenzene was 29.2%.

TABLE 18

| | |
|---|---|
| Isobutylbenzene | 60.3% by weight |
| Isobutylethylbenzene | 27.3% by weight |
| ortho- | 9.7% by weight |
| meta- | 8.8% by weight |
| para- | 8.8% by weight |
| Isobutyldiethylbenzene | 9.3% by weight |
| Others | 3.1% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 32 g (recovery 72.7%).

EXPERIMENTAL EXAMPLE 21

In a 1-liter autoclave were placed 500 g of the mixture of the components in Table 12 and 25 g of hydrogen fluoride, and reaction was then carried out with stirring at 110° C. for 12 hours under an ethylene pressure of 20 kg/cm². Afterward, the reaction mixture was neutralized with Ca(OH)₂, washed with water, and the resultant organic phase was then analyzed by a gas chromatography. The results are set forth in Table 19. In consequence, the conversion of isobutylbenzene was 26.0%, and the selectivity coefficient of p-isobutylethylbenzene was 29.5%.

TABLE 19

| Isobutylbenzene | 60.5% by weight |
|---|---|
| Isobutylethylbenzene | 27.0% by weight |
| ortho- | 9.3% by weight |
| meta- | 8.9% by weight |
| para- | 8.8% by weight |
| Isobutyldiethylbenzene | 9.4% by weight |
| Others | 3.1% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 31 g (recovery 70.5%).

EXPERIMENTAL EXAMPLE 22

In a 1-liter autoclave were placed 500 g of the mixture of the components in Table 12 and 25 g of phosphotungstic acid, and reaction was then carried out with stirring at 250° C. for 12 hours under an ethylene pressure of 20 kg/cm². Afterward, the used catalyst was removed from the reaction mixture by filtration, and the resultant organic phase was then analyzed by a gas chromatography. The results are set forth in Table 20. In consequence, the conversion of isobutylbenzene was 24.9%, and the selectivity coefficient of p-isobutylethylbenzene was 26.8%.

TABLE 20

| Isobutylbenzene | 61.4% by weight |
|---|---|
| Isobutylethylbenzene | 24.9% by weight |
| ortho- | 9.1% by weight |
| meta- | 8.0% by weight |
| para- | 7.8% by weight |
| Isobutyldiethylbenzene | 9.4% by weight |
| Others | 4.3% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 26 g (recovery 66.7%).

EXPERIMENTAL EXAMPLE 22A

In a 1-liter autoclave were placed 500 g of the mixture of the components in Table 12 and 25 g of HX zeolite, and reaction was then carried out with stirring at 160° C. for 12 hours under an ethylene pressure of 20 kg/cm². Afterward, the used catalyst was removed from the reaction mixture by filtration, and the resultant organic phase was then analyzed by a gas chromatography. The results are set forth in the following table. In consequence, the conversion of isobutylbenzene was 26.8%, and the selectivity coefficient of p-isobutylethylbenzene was 22.2%.

TABLE

| Isobutylbenzene | 62.4% by weight |
|---|---|
| Isobutylethylbenzene | 22.3% by weight |
| ortho- | 8.8% by weight |
| meta- | 7.1% by weight |
| para- | 6.4% by weight |
| Isobutyldiethylbenzene | 11.2% by weight |
| Others | 4.1% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 22 g (recovery 68.8%).

EXPERIMENTAL EXAMPLE 22B

In a 1-liter autoclave were placed 500 g of the mixture of the components in Table 12 and 25 g of HY zeolite, and reaction was then carried out with stirring at 170° C. for 12 hours under an ethylene pressure of 20 kg/cm². Afterward, the used catalyst was removed from the reaction mixture by filtration, and the resultant organic phase was then analyzed by a gas chromatography. The results are set forth in the following table. In consequence, the conversion of isobutylbenzene was 28.8%, and the selectivity coefficient of p-isobutylethylbenzene was 23.1%.

TABLE

| Isobutylbenzene | 58.2% by weight |
|---|---|
| Isobutylethylbenzene | 26.0% by weight |
| ortho- | 9.7% by weight |
| meta- | 8.5% by weight |
| para- | 7.8% by weight |
| Isobutyldiethylbenzene | 10.1% by weight |
| Others | 5.7% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 28 g (recovery 71.8%).

EXPERIMENTAL EXAMPLE 22C

In a 1-liter autoclave were placed 500 g of the mixture of the components in Table 12 and 25 g of hydrogen faujasite, and reaction was then carried out with stirring at 200° C. for 12 hours under an ethylene pressure of 20 kg/cm². Afterward, the used catalyst was removed from the reaction mixture by filtration, and the resultant organic phase was then analyzed by a gas chromatography. The results are set forth in the following table. In consequence, the conversion of isobutylbenzene was 28.7%, and the selectivity coefficient of p-isobutylethylbenzene was 23.2%.

TABLE

| Isobutylbenzene | 58.3% by weight |
|---|---|
| Isobutylethylbenzene | 23.3% by weight |
| ortho- | 8.3% by weight |
| meta- | 7.2% by weight |
| para- | 7.8% by weight |
| Isobutyldiethylbenzene | 10.8% by weight |
| Others | 7.6% by weight |

This reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 27 g (recovery 69.2%).

EXPERIMENTAL EXAMPLE 23

In a 10-liter three-necked flask were placed 5 kg of a mixture of o-isobutylethylbenzene:m-isobutylethylbenzene:p-isobutylethylbenzene=40:47:13 and 1 kg of 1,1-bis(p-isobutylphenyl)ethane, and distillation was then carried out on a batch system by the use of a distillation column in which the number of theoretical plates was 24, the aforesaid distillation column being composed of a glass pipe having an inner diameter of 30 mm and a length of 1.0 m which was packed with a filler, Heli Pack No. 3 metal made by Tokyo Tokushu Kanaami Co., Ltd. In this case, a fraction of p-isobutylethylbenzene having a purity of 97% by weight or more was prepared in an amount of 126 g (recovery 19.4%).

EXPERIMENTAL EXAMPLE 23A

In a 1-liter autoclave were placed 600 ml of isobutylbenzene having 99.8% by weight purity and 30 g of NAFION resin pellets (trade name; made by Du Pont; diameter=1 mm and length=3-5 mm), and the temperature in the system was then raised up to 180° C. while stirring. Afterward, ethylene was fed thereto, and reaction was then performed for 12 hours, while the pressure in the autoclave was maintained at 20 kg/cm². After the completion of the reaction, the used catalyst was removed by filtration and the resultant reaction mixture was then analyzed by a gas chromatography. The composition of the reaction mixture is set forth in the following table.

TABLE

| Isobutylbenzene | 52.9% by weight |
|---|---|
| Isobutylethylbenzene | 20.7% by weight |
| ortho- | 7.9% by weight |
| meta- | 5.9% by weight |
| para- | 6.9% by weight |
| Isobutyldiethylbenzene | 11.4% by weight |
| Others | 15.0% by weight |

As a result, the conversion of isobutylbenzene was 47.0% by weight, the selectivity coefficient of p-isobutylethylbenzene was 12.2%, and position isomers of isobutylethylbenzene were present in a ratio of o:m:p=38:29:33.

EXPERIMENTAL EXAMPLE 23B

Following the same procedure as in Experimental Example 15, 500 g of the mixture of the components in Table 12 and 30 g of NAFION resin pellets (trade name; made by Du Pont; diameter=1 mm and length=3-5 mm) were placed in a 1-liter autoclave, and reaction was then carried out at 180° C. for 24 hours under stirring. Afterward, the used catalyst was removed from the reaction mixture by filtration, and the resultant organic phase was then analyzed by a gas chromatography. The results are set forth in the following table.

TABLE

| Isobutylbenzene | 77.4% by weight |
|---|---|
| Isobutylethylbenzene | 15.4% by weight |
| ortho- | 2.0% by weight |
| meta- | 7.6% by weight |
| para- | 5.8% by weight |
| Isobutyldiethylbenzene | 2.6% by weight |
| Others | 4.6% by weight |

The disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 20 g (recovery 69.0%).

EXPERIMENTAL EXAMPLE 23C

In a 1-liter autoclave were placed 500 g of the mixture of the components in Table 12 and 30 g of NAFION resin pellets (trade name; made by Du Pont; diameter=1 mm and length=3-5 mm), and reaction was then carried out with stirring at 180° C. for 12 hours under an ethylene pressure of 20 kg/cm². Afterward, the used catalyst was removed from the reaction mixture by filtration, and the resultant organic phase was then analyzed by a gas chromatography. The results are set forth in the following table. As a result, the conversion of isobutylbenzene was 43.5%, and the selectivity coefficient of p-isobutylethylbenzene was 21.8%.

TABLE

| Isobutylbenzene | 46.2% by weight |
|---|---|
| Isobutylethylbenzene | 34.3% by weight |
| ortho- | 11.7% by weight |
| meta- | 12.0% by weight |
| para- | 10.6% by weight |
| Isobutyldiethylbenzene | 10.3% by weight |
| Others | 9.2% by weight |

This disproportionated reaction mixture was placed in a 1-liter three-necked flask, and distillation was then performed in the same manner as in Experimental Example 14. In this case, a fraction of p-isobutylethylbenzene having a purity of 97% by weight or more was prepared in an amount of 40 g (recovery 75.5%).

Experimental Examples of Side Chain Alkylation

Step IB

EXPERIMENTAL EXAMPLE 24

In a 0.5-liter pressure-resistant reactor equipped with a stirrer were placed 180 g (1.5 moles) of 4-ethyltoluene, 0.6 g (0.026 mole) of solid sodium metal, 6 g (0.043 mole) of potassium carbonate powder and 0.054 g (0.52 millimole) of styrene, and the reactor was heated up to 180° C. with stirring After the heating, the reactor was pressurized to 40 kg/cm² with propylene, and reaction was then performed for 24 hours. After the completion of the reaction, the reactor was cooled to room temperature, and unreacted propylene was separated and removed. Afterward, 10 ml of methyl alcohol was added to the solution, and the latter was then stirred for 30 minutes in order to inactivate sodium. In addition, the solution was washed with water, until the wash liquid had become neutral, so that 280 g of an oily mixture was obtained.

The oily mixture was then distilled to obtain 54 g of a hexene fraction which was a dimer of propylene having a running temperature of 60°-70° C., 25 g of the raw material 4-ethyltoluene fraction having a running temperature of 160°-170° C., 148 g of a fraction containing the desired component 4-isobutylethylbenzene having a running temperature of 195°-215° C., and 53 g of a distillation residue.

EXPERIMENTAL EXAMPLES 25 TO 27

Following the same procedure as in Experimental Example 24, 4-ethyltoluene was reacted with propylene to obtain the following results.

TABLE

| Example | Catalyst (g) | Reaction Temp. (°C.) | Desired Fraction (g) |
|---|---|---|---|
| 25 | sodium (0.6) potassium carbonate (6) | 180 | 129 |
| 26 | sodium (1) | 210 | 101 |
| 27 | potassium (1) | 150 | 124 |

Preparation of p-Isobutylstyrene

Dehydrogenation Step II

EXPERIMENTAL EXAMPLE 28

A dehydrogenation catalyst of iron oxide containing potassium and chromium as well as promotors (trade namde G-64A; Nissan Gardlar Co., Ltd.) were ground so that the particle diameter of the resultant powder might be in the range of 1 to 2 mm, and a stainless steel pipe having an inner diameter of 12 mm and a length of 1 m was packed with 20 ml of the above-mentioned powder.

p-Isobutylethylbenzene (hereinafter referred to as "PBE" sometimes) and water were passed, at flow rates of 10 ml/hr and 90 ml/hr, respectively, through a preheater pipe and the catalyst layer in the pipe at a temperature of 550° C., and dehydrogenation was then carried out (contact time with the catalyst=0.2 second; molar ratio of steam to p-isobutylethylbenzene=93). The dehydrogenated material was then cooled, and a gas and water were separated and removed therefrom. Afterward, the resultant organic phase was analyzed by a gas chromatography in order to inspect the conversion of p-isobutylethylbenzene and the selectivity coefficient of p-isobutylstyrene (hereinafter referred to as PBS at times).

It was confirmed that the organic phase of the dehydrogenated substance was mainly composed of PBE, PBS, 4-(2'-methyl-1'-propenyl)ethylbenzene (hereinafter referred to as "1-MPE" sometimes), 4-(2'-methyl-2'-propenyl)ethylbenzene (hereinafter referred to as "2-MPE" sometimes), 4-(2'-methyl-1'-propenyl)vinylbenzene (hereinafter referred to as "1-MPV" sometimes) and 4-(2'-methyl-2'-propenyl)vinylbenzene (hereinafter referred to as "2-MPV" sometimes). The composition of the organic phase is set forth in Table 21.

TABLE 21

| Component | Content |
|---|---|
| PBE | 69.3% by weight |
| PBS | 24.7% by weight |
| 1-MPE | 0.6% by weight |
| 2-MPE | 1.6% by weight |
| 1-MPV | 0.9% by weight |
| 2-MPV | 2.1% by weight |
| unidentified | 0.8% by weight |

From these data, it is apparent that the conversion of PBE was 31% and the selectivity coefficient of PBS was 83%, and it was confirmed that PBS was formed in the high selectivity coefficient by the dehydrogenation.

Afterward, the dehydrogenated material was separated into constitutional components, and they were analyzed by means of mass sepctrometry, infrared spectrophotometry and NMR. As a result, p-isobutylethylbenzene was identical with that which was used as the raw material, and the production of sec-butylbenzene and tert-butylbenzene was not perceived. Then, it could be confirmed that seconday reactions such as the isomerization of an isobutyl group did not occur, and that the butyl group in PBS is an isobutyl group and this group was present at the p-position.

EXPERIMENTAL EXAMPLES 29 TO 32

Following the same procedure as in Experimental Example 28, dehydrogenation was carried out, changing reaction temperatures. The obtained results are set forth together with the results of Experimental Example 28 in Table 22.

TABLE 22

|  | Experimental Example | | | | |
|---|---|---|---|---|---|
|  | 29 | 30 | 28 | 31 | 32 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 94 | 92 | 93 | 94 |
| Conversion of PBE (%) | 1 | 6 | 31 | 75 | 96 |
| Selectivity of PBS (%) | 99 | 98 | 83 | 51 | 7 |

EXPERIMENTAL EXAMPLES 33 TO 37

Following the same procedure as in Experimental Example 28, dehydrogenation was carried out, changing contact times. The results are set forth in Table 23.

TABLE 23

|  | Experimental Example | | | | |
|---|---|---|---|---|---|
|  | 33 | 34 | 35 | 36 | 37 |
| Reaction Temp. (°C.) | 550 | 550 | 550 | 550 | 550 |
| Contact Time (sec) | 0.06 | 0.10 | 0.21 | 0.28 | 0.38 |
| Molar Ratio of Steam | 96 | 98 | 96 | 94 | 96 |
| Conversion of PBE (%) | 21 | 33 | 37 | 47 | 54 |
| Selectivity of PBS (%) | 89 | 84 | 79 | 73 | 69 |

EXPERIMENTAL EXAMPLES 38 TO 42

Following the same procedure as in Experimental Example 28, dehydrogenation was carried out, using a copper-chromium dehydrogenation catalyst comprising 43% by weight of CuO, 42% by weight of $Cr_2O_3$ and 15% by weight of $SiO_2$, reaction temperatures being changed. The results are set forth in Table 24.

TABLE 24

|  | Experimental Example | | | | |
|---|---|---|---|---|---|
|  | 38 | 39 | 40 | 41 | 42 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 94 | 92 | 93 | 94 |
| Conversion of PBE (%) | 5 | 8 | 20 | 50 | 92 |
| Selectivity of PBS (%) | 80 | 79 | 74 | 58 | 5 |

EXPERIMENTAL EXAMPLES 43 TO 47

Following the same procedure as in Experimental Example 28, dehydrogenation was carried out, using a copper-chromium dehydrogenation catalyst comprising 18% by weight of $Cr_2O_3$, 39% by weight of CuO and 38% by weight of ZnO. The results are set forth in Table 25.

TABLE 25

|  | Experimental Example | | | | |
|---|---|---|---|---|---|
|  | 43 | 44 | 45 | 46 | 47 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 93 | 94 | 93 | 93 |
| Conversion of PBE (%) | 2 | 6 | 12 | 21 | 45 |
| Selectivity of PBS (%) | 78 | 76 | 72 | 64 | 47 |

EXPERIMENTAL EXAMPLE 47A

Following the same procedure as in Experimental Example 28, dehydrogenation of PBE was carried out, changing metals of the dehydrogenation metal catalysts as in the following table. All of the metals were used in the form of oxides, and each metal was supported in silica. The results are set forth in the following table.

TABLE

| Metal | Conversion (%) | Selectivity (%) |
|---|---|---|
| Ag | 31 | 62 |
| Cd | 12 | 64 |
| Cr | 22 | 61 |
| Zn | 13 | 52 |
| Mo | 16 | 53 |
| W | 11 | 59 |
| Mn | 11 | 61 |
| Tc | 12 | 60 |
| Re | 20 | 57 |
| Ru | 17 | 68 |
| Os | 12 | 70 |
| Co | 21 | 59 |
| Rh | 32 | 48 |
| Ir | 25 | 51 |
| Ni | 48 | 41 |
| Pd | 46 | 43 |
| Pt | 44 | 40 |

Hydroformylation Step (step IIIA)

EXPERIMENTAL EXAMPLE 48

In a 100-ml autoclave equipped with a stirrer were placed 30 g of p-isobutylstyrene having 97.8% by weight purity obtained by distilling/purifying the organic phase of the dehydrogenated material in Experimental Example 28, and 0.3 g of rhodium hydride carbonyltristriphenylphosphine. The temperature in the autoclave was then elevated up to 60° C. with stirring, and the pressure therein was increased to 50 kg/cm$^2$ by an equimolar mixed gas of hydrogen and carbon monoxide. Afterward, reaction was performed until the mixed gas had not been absorbed any more.

After the completion of the reaction, the reaction mixture was cooled to room temperature, and was then analyzed by a gas chromatography. As a result, it was confirmed that the conversion of p-isobutylstyrene was 99.9% and the selectivity coefficient of α-(4-isobutylphenyl)propionaldehyde was 88.7%.

EXPERIMENTAL EXAMPLE 49

Following the same procedure as in Experimental Example 48 with the exception that rhodium hydride carbonyltristriphenylphosphine was replaced with 0.1 g of rhodium oxide and 0.6 g of triphenylphosphine, experiment was carried out. As a result, the conversion of p-isobutylstyrene was 99.9%, and the selectivity coefficient of α-(4-isobutylphenyl)propionaldehyde was 82.2%.

EXPERIMENTAL EXAMPLE 50

In a 200-ml autoclave equipped with a stirrer were placed 121.5 g of the organic phase of the dehydrogenated material obtained in Experimental Example 28 and 0.3 g of rhodium hydride carbonyltristriphenylphosphine, and the same procedure as in Experimental Example 48 was repeated. As a result, the conversion of p-isobutylstyrene was 99.8%, the selectivity coefficient of α-(4-isobutylphenyl)propionaldehyde was 87.8%, the hydroformylation of the substituted propenyl group of 4-(2'-methyl-1'-propenyl)ethylbenzene was 0%, the hydroformylation of the substituted propenyl group of 4-(2'-methyl-2'-propenyl)ethylbenzene was 0.4%, the hydroformylation of the substituted propenyl group of 4-(2'-methyl-1'-propenyl)vinylbenzene was 0%, and the hydroformylation of the substituted propenyl group of 4-(2'-methyl-2'-propenyl)vinylbenzene was 0.1%.

Preparation of α-(4-isobutylphenyl)propionic acid by oxidation of α-(4-isobutylphenyl)propionaldehyde

EXPERIMENTAL EXAMPLE 51

In a 100-ml flask equipped with a stirrer was placed 10 g of α-(4-isobutylphenyl)propionaldehyde having a boiling point of 70 to 76° C./3 mmHg obtained by distilling the reaction mixture of Experimental Example 50 under reduced pressure, and 0.4 g of concentrated hydrochloric acid and 16 ml of acetone as a solvent were further added thereto. Afterward, the mixture was cooled to −15° C. Next, while the temperature of the mixture was maintained in the range of −12° to −16° C., 36 g of a 10% aqueous sodium hypochlorite solution was gradually added dropwise thereto. After the completion of the addition, reaction was performed for 1 hour with stirring. After the reaction had been over, the mixture was neutralized with a 5% aqueous sodium hydroxide solution, so that its pH was adjusted to 8.5. The mixture was then allowed to stand, and the resultant lower layer, i.e., water phase was washed with normal hexane. Afterward, a 5% hydrochloric acid solution was added to the water phase in order to adjust its pH to 2, and a separated oil phase was then extracted with normal hexane and washed with water. Normal hexane was vaporized and removed under reduced pressure, thereby obtaining 9.3 g of light yellow crude α-(4-isobutylphenyl)propionic acid crystals.

Crude α-(4-isobutylphenyl)propionic acid was then recrystallized with a normal hexane solvent in order to obtain 7.5 g of white purified α-(4-isobutylphenyl)propionic acid (melting point=75°-76° C.). Spectra and the like of this product were in accord with the standards.

Hydroesterification and hydrocarboxylation step

Step IIIB

EXPERIMENTAL EXAMPLE 52

Hydrocarboxylation

In a 500-ml autoclave were placed 50 g of p-isobutylstyrene having 97.8% by weight purity obtained by distilling/purifying the organic phase of the dehydrogenated material in Experimental Example 28, 5.5 g of bisdichlorotriphenylphosphine palladium, 80 g of a 10% aqueous hydrochloric acid solution and 80 ml of toluene as a solvent. Afterward, the pressure in the autocalve was increased up to 100 kg/cm$^2$ at ordinary temperature with stirring by the use of carbon monoxide, and while the temperature in the autoclave was elevated up to 120° C., the pressure therein was further increased up to 300 kg/cm$^2$. After reaction proceeded and carbon monoxide had not been absorbed any more, the reaction was further continued for 24 hours.

After the completion of the reaction, cooling followed in order to recover the reaction mixture, and the resultant oil layer and water layer were separated from each other by a separating funnel. The oil layer was then subjected to extraction three times by the use of 50 ml of a 8% aqueous sodium hydroxide solution, and an extracted aqueous solution was then mixed with the separated water layer. Hydrochloric acid was then added thereto so as to adjust the pH of the solution to 2. Afterward, extraction was performed three times with 500 ml of chloroform, and chloroform was then distilled off from the extract under reduced pressure, thereby obtaining 52.3 g of light yellow α-(4-isobutylphenyl)propionic acid crystals. In this case, the conversion of p-isobutylstyrene was 100%, and the selectivity coefficient of α-(4-isobutylphenyl)propionic acid was 89.0%.

EXPERIMENTAL EXAMPLE 53

In a 500-ml autoclave were placed 202.43 g of the organic phase of the dehydrogenated material obtained in Experimental Example 28, 5.5 g of bisdichlorotriphenylphosphine palladium and 80 g of a 10% aqueous hydrochloric acid solution. Afterward, the pressure in the autocalve was increased up to 100 kg/cm$^2$ at ordinary temperature with stirring by the use of carbon monoxide, and while the temperature in the autoclave was elevated up to 120° C., the pressure therein was further increased up to 300 kg/cm$^2$. After reaction proceeded and carbon monoxide had not been absorbed any more, the reaction was further continued for 24 hours.

After the completion of the reaction, cooling followed in order to recover the reaction mixture, and the resultant oil layer and water layer were separated from each other by a separating funnel. The oil layer was then subjected to extraction three times by the use of 50 ml of a 8% aqueous sodium hydroxide solution, and an extracted aqueous solution was then mixed with the separated water layer. Hydrochloric acid was then added thereto so as to adjust the pH of the solution to 2. Afterward, extraction was performed three times with 500 ml of chloroform, and chloroform was then distilled off from the extract under reduced pressure, thereby obtaining 50.2 g of light yellow α-(4-isobutylphenyl)propionic acid crystals. In this case, the conversion of p-isobutylstyrene was 100%, the selectivity coefficient of α-(4-isobutylphenyl)propionic acid was 87.3%, the hydrocarboxylation of the substituted propenyl group of 4-(2'-methyl-1'-propenyl)ethylbenzene was 0%, the hydrocarboxylation of the substituted propenyl group of 4-(2'-methyl-2'-propenyl)ethylbenzene was 0.8%, the hydrocarboxylation of the substituted propenyl group of 4-(2'-methyl-1'-propenyl)vinylbenzene was 0%, and the hydrocarboxylation of the substituted propenyl group of 4-(2'-methyl-2'-propenyl)vinylbenzene was 0.6%.

EXPERIMENTAL EXAMPLE 54

Hydroesterification

In a 200-ml autoclave were placed 70.4 g of p-isobutylstyrene having 97.8% by weight purity obtained by distilling/purifying the organic phase of the dehydrogenated material in Experimental Example 28, 25.5 ml of methanol, 40 ml of toluene as a solvent, 0.0756 g of PdCl$_2$ as a catalyst, 0.0292 g of CuCl$_2$ as a promotor and 0.2161 g of triphenylphosphine as a ligand. The temperature in the autoclave was then elevated up to 90° C. under stirring, and reaction was performed for 8 hours, while the pressure in the autoclave was maintained at 70 kg/cm$^2$ with carbon monoxide. After the completion of the reaction, cooling followed, and the reaction mixture was then analyzed by means of a gas chromatography. As a result, the conversion of p-isobutylstyrene was 99.6%, the selectivity coefficient of methyl α-(4-isobutylphenyl)propionate was 90.9%.

EXPERIMENTAL EXAMPLE 55

In a 500-ml autoclave were placed 285.0 g of the organic phase obtained in Experimental Example 28, 25.5 ml of methanol, 0.0756 g of PdCl$_2$ as a catalyst, 0.0292 g of CuCl$_2$ as a promotor and 0.2161 g of triphenylphosphine as a ligand. The temperature in the autoclave was then elevated up to 90° C. under stirring, and reaction was performed for 8 hours, while the pressure in the autoclave was maintained at 70 kg/cm$^2$ with carbon monoxide. After the completion of the reaction, cooling followed, and the reaction mixture was then analyzed by means of a gas chromatography. As a result, the conversion of p-isobutylstyrene was 99.8%, the selectivity coefficient of methyl α-(4-isobutylphenyl)propionate was 88.9%, the hydroesterification of the substituted propenyl group of 4-(2'-methyl-1'-propenyl)ethylbenzene was 0%, the hydroesterification of the substituted propenyl group of 4-(2'-methyl-2'-propenyl)ethylbenzene was 0.6%, the hydroesterification of the substituted propenyl group of 4-(2'-methyl-1'-propenyl)vinylbenzene was 0%, and the hydroesterification of the substituted propenyl group of 4-2'-methyl-2'-propenyl)vinylbenzene was 0.3%.

Preparation of α-(4-isobutylphenyl)propionic acid by hydrolyzing methyl α-(4-isobutylphenyl)propionate

EXPERIMENTAL EXAMPLE 56

Thirty grams of methyl α-(4-isobutylphenyl)propionate in Experimental Example 54 and 150 ml of a 10% aqueous sodium hydroxide solution were refluxed with stirring for about 3 hours in order to perform hydrolysis. After cooling, the mixture was allowed to stand, and the separated lower layer, i.e., water phase was then washed with normal hexane.

A 5% hydrochloric acid solution was added to the water phase so as to adjust its pH to 2, and the separated oil was then extracted with normal hexane and washed with water. Afterward, normal hexane was vaporized/removed under reduced pressure, and thereby obtaining 23.9 g of light yellow crude α-(4-isobutylphenyl)propionic acid crystals.

Crude α-(4-isobutylphenyl)propionic acid was then recrystallized with a normal hexane solvent in order to obtain 20.7 g of white purified α-(4-isobutylphenyl)propionic acid (melting point=75°-76° C.). Spectra and the like of this product were in accord with the standards.

EXPERIMENTAL EXAMPLE 57

One hundred grams of the hydroesterified reaction mixture in Experimental Example 55 and 150 ml of a 10% aqueous sodium hydroxide solution were refluxed with stirring for about 3 hours in order to perform hydrolysis. After cooling, the mixture was allowed to stand, and the separated lower layer, i.e., water phase was then washed with normal hexane.

A 5% hydrochloric acid solution was added to the water phase so as to adjust its pH to 2, and the separated oil was then extracted with normal hexane and washed with water. Afterward, normal hexane was vaporized/removed under reduced pressure, and thereby obtaining 22.4 g of light yellow crude α-(4-isobutylphenyl)propionic acid crystals.

Crude α-(4-isobutylphenyl)propionic acid was then recrystallized with a normal hexane solvent in order to obtain 19.9 g of white purified α-(4-isobutylphenyl)propionic acid (melting point=75°-76° C.). Spectra and the like of this product were in accord with the standards.

EXPERIMENTAL EXAMPLE 58

Synthesis of o-isobutylethylbenzene

In a 7-liter separable four-necked flask equipped with a stirrer and a reflux condenser were placed 3 liters of sufficiently dried diethyl ether and 245 g of metallic magnesium, and 1,370 g (10 moles) of isobutyl bromide was then added thereto slowly dropwise, while diethyl ether was refluxed. After the completion of the addition, stirring was performed for 1 hour under the reflux of diethyl ether, and the resultant diethyl ether solution of isobutylmagnesium bromide was transferred into a dropping funnel.

In a 15-liter separable four-necked flask equipped with a stirrer and a reflux condenser were placed 3 liters of sufficiently dried diethyl ether, 915 g (5 moles) of o-bromostyrene and 31 g of bis(1,3-diphenylphosphino)propanenickel(II) chloride, and the above-mentioned diethyl ether solution of isobutylmagnesium bromide was added thereto dropwise with stirring at room temperature. After the completion of the addition, stirring was continued under the reflux of diethyl ether, until the reaction had been over. After the end of the reaction, the solution was cooled to room temperature, and was then thrown into pieces of ice in order to inactivate remaining isobutylmagnesium bromide. The resultant ether layer was separated by a separating funnel, and was washed with water until it had become a neutral state. Afterward, diethyl ether was distilled off, thereby obtaining 716 g of crude o-isobutylstyrene.

In a 1-liter autoclave equipped with a stirrer were placed 35.8 g of a 10% palladium black catalyst and all of the above-mentioned crude o-isobutylstyrene, and hydrogenation was carried out at a reaction temperature of 50° C. under a hydrogen pressure of 20 kg/cm². After hydrogen had not been absorbed any more, the used catalyst was removed from the reaction mixture by filtration, followed by distillation, thereby obtaining 642 g of o-isobutylethylbenzene having 99.8% purity.

Physical properties of o-isobutylethylbenzene:
Boiling point (static method): 211.1° C. (colorless liquid)
Specific gravity (Ostwald's pycnometer method; 15/4° C.) 0.8724
Refractive index $(N_{20}{}^D)$: 1.4956
Kinematic viscosity (40° C.): 1.46CS
Infrared absorption spectrum (liquid film method; $cm^{-1}$): 2960, 1950, 1920, 1850, 1820, 1700, 1610, 1500, 1470, 1390, 1370, 1340, 1290, 1170, 1140, 1080, 1070, 970, 940, 920, 800, 760
NMR spectrum (CCl₄ solvent; δppm): 6.95 (4H, singlet), 2.3-2.8 (4H, quartet), 1.5-2.1 (1H, septet), 1.0-1.4 (3H, triplet), 0.7-1.0 (6H, doublet).
Mass spectrometry spectrum (EI, 70 eV):

| m/e | (pattern coefficient) |
|---|---|
| 162 | (31) |
| 133 | (5) |
| 119 | (100) |
| 105 | (14) |
| 91 | (24) |
| 77 | (7) |
| 43 | (5) |
| 29 | (2) |

Elementary analysis (as $C_{12}H_{18}$): Theoretical value C: 88.89, H: 11.11, Analytical value C: 88.92, H: 10.97.

EXPERIMENTAL EXAMPLES 59

Synthesis of m-isobutylethylbenzene

In a 7-liter separable four-necked flask equipped with a stirrer and a reflux condenser were placed 3 liters of sufficiently dried diethyl ether and 245 g of metallic magnesium, and 1,370 g (10 moles) of isobutyl bromide was then added thereto slowly dropwise, while diethyl ether was refluxed. After the completion of the addition, the solution was stirred for 1 hour under the reflux of diethyl ether, and the resultant diethyl ether solution of isobutylmagnesium bromide was transferred into a dropping funnel.

In a 15-liter separable four-necked flask equipped with a stirrer and a reflux condenser were placed 3 liters of sufficiently dried diethyl ether, 915 g (5 moles) of m-bromostyrene and 31 g of bis(1,3-diphenylphosphino)propanenickel(II) chloride, and the above-mentioned diethyl ether solution of isobutylmagnesium bromide was added thereto dropwise with stirring at room temperature. After the completion of the addition, stirring was continued under the reflux of diethyl ether, until the reaction had been over. After the end of the reaction, the solution was cooled to room temperature, and was then thrown into pieces of ice in order to inactivate remaining isobutylmagnesium bromide. The resultant ether layer was separated by a separating funnel, and was washed with water until it had become a neutral state. Afterward, diethyl ether was distilled off, thereby obtaining 670 g of crude m-isobutylstyrene.

In a 1-liter autoclave equipped with a stirrer were placed 33.5 g of a 10% palladium black catalyst and all of the above-mentioned crude m-isobutylstyrene, and hydrogenation was carried out at a reaction temperature of 50° C. under of 20 kg/cm². After hydrogen had not been absorbed any more, the used catalyst was removed from the reaction mixture by filtration, followed by distillation, thereby obtaining 617 g of m-isobutylethylbenzene having 99.7% purity.

Physical properties of m-isobutylethylbenzene:
Boiling point (static method): 210.8° C. (colorless liquid)
Specific gravity (Ostwald's pycnometer method; 15/4° C.) 0.8583
Refractive index ($N_{20}^D$): 1.4884
Kinematic viscosity (40° C.): 1.29CS
Infrared absorption spectrum (liquid film method; $cm^{-1}$): 2960, 1940, 1860, 1800, 1700, 1620, 1590, 1500 1470, 1390, 1370, 1340, 1290, 1220, 1180, 1110 1090, 1070, 1060, 890, 820, 790, 740, 710
NMR spectrum ($CCl_4$ solvent; δppm): 6.95 (4H, singlet), 2.3-2.8 (4H, quartet), 1.5-2 1 (1H, septet), 1.0-1.4 (3H, triplet), 0.7-1.0 (6H, doublet).
Mass spectrometry spectrum (EI, 70 eV):

| m/e | (pattern coefficient) |
|---|---|
| 162 | (35) |
| 133 | (2) |
| 119 | (100) |
| 105 | (19) |
| 91 | (24) |
| 77 | (6) |
| 43 | (7) |
| 29 | (2) |

Elementary analysis (as $C_{12}H_{18}$): Theoretical value C: 88.89, H: 11.11, Analytical value C: 88.91, H: 10.99.

EXPERIMENTAL EXAMPLE 60

Preparation of p-isobutylethylbenzene

Disproportionation Reaction 1

In a 3-liter autoclave equipped with a stirrer were placed 600 g of o-isobutylethylbenzene obtained in Experimental Example 58, 1,200 g of isobutylbenzene having 99.8% purity and 90 g of a silica-alumina catalyst N633L (trade name; made by Nikki Chemicals Co., Ltd.), and the gaseous portion in the system was replaced with nitrogen. Afterward, the system was sealed up and its temperature was elevated to 270° C., and disproportionation reaction was then carried out for 24 hours. After the completion of the reaction, the used catalyst was eliminated therefrom by filtration, and the reaction mixture was then analyzed by means of a gas chromatography. The composition of the reaction mixture is set forth in the following table.

TABLE

| Isobutylbenzene | 59.2% by weight |
|---|---|
| o-Isobutylethylbenzene | 7.8% by weight |
| m-Isobutylethylbenzene | 12.3% by weight |
| p-Isobutylethylbenzene | 7.9% by weight |
| Others | 12.8% by weight |

The conversion of o-isobutylethylbenzene was 76.6%, and the selectivity coefficient of p-isobutylethylbenzene was 31.0%.

EXPERIMENTAL EXAMPLE 61

Preparation of p-isobutylethylbenzene

Disproportionation Reaction 2

In a 3-liter autoclave equipped with a stirrer were placed 600 g of m-isobutylethylbenzene obtained in Experimental Example 59, 1,200 g of isobutylbenzene having 99.8% purity and 90 g of a silica-alumina catalyst N633L (trade name; made by Nikki Chemicals Co., Ltd.), and the gaseous portion in the system was then replaced with nitrogen. Afterward, the system was sealed up and its temperature was raised up to 270° C., and disproportionation reaction was then carried out for 24 hours. After the completion of the reaction, the used catalyst was eliminated therefrom by filtration, and the reaction mixture was then analyzed by means of a gas chromatography. The composition of the reaction mixture is set forth in the following table.

TABLE

| Isobutylbenzene | 58.9% by weight |
|---|---|
| o-Isobutylethylbenzene | 6.7% by weight |
| m-Isobutylethylbenzene | 15.4% by weight |
| p-Isobutylethylbenzene | 6.0% by weight |
| Others | 13.0% by weight |

The conversion of m-isobutylethylbenzene was 53.7%, and the selectivity coefficient of p-isobutylethylbenzene was 22.6%.

EXPERIMENTAL EXAMPLE 62

Preparation of p-isobutylethylbenzene

Distillation 1

In a 3-liter three-necked flask was placed 1,800 g of the reaction mixture obtained in Experimental Example 60, and distillation was then carried out on a batch system by the use of a distillation column in which the number of theoretical plates was 35, the aforesaid distillation column being composed of a glass pipe having an inner diameter of 30 mm and a length of 1.5 m which was packed with a filler, Heli Pack No. 3 metal (trade name) made by Tokyo Tokushu Kanaami Co., Ltd. In this case, a fraction of p-isobutylethylbenzene having 97.2% purity was prepared in an amount of 92.1 g (recovery 63.0%).

EXPERIMENTAL EXAMPLE 63

Preparation of p-isobutylethylbenzene

Distillation 2

According to the same procedure as in Experimental Example 62, 1,800 g of a reaction mixture obtained in Experimental Example 61 was distilled. In this case, a fraction of p-isobutylethylbenzene having 97.4% purity was prepared in an amount of 68.3 g (recovery 61.6%).

EXPERIMENTAL EXAMPLE 64

Preparation of p-isobutylstyrene

Dehydrogenation Reaction

An iron oxide catalyst for dehydrogenation containing potassium and chromium as promotors, G-64A (trade name; made by Nissan Gardlar Co., Ltd.) was ground so that the grain diameter of the resultant powder might be in the range of 1 to 2 mm, and a stainless steel pipe having an inner diameter of 12 mm and a length of 1 m was packed with 20 ml of this powder.

Afterward, dehydrogenation was carried out by passing water and 160.4 g of a mixture of the p-isobutylethylbenzene fractions (purity of p-isobutylethylbenzene=97.3%) obtained in Experimental Example Nos. 62 and 63 through a preheater pipe and the catalyst layer at flow rates of 90 ml/hr and 10 ml/hr, respectively, at a reaction temperature of 550° C. (contact time with the catalyst=0.2 second; molar ratio of steam to p-isobutylethylbenzene=93). The dehydrogenated material was then cooled, and a gas and water were separated therefrom. The resultant organic phase was then analyzed by a gas chromatography. The composition of the organic phase is set forth in the following table.

TABLE

| | |
|---|---|
| p-Isobutylethylbenzene | 69.1% by weight |
| p-Isobutylstyrene | 23.2% by weight |
| Others | 7.7% by weight |

It was apparent from these data that the conversion of p-isobutylethylbenzene was 29.0% by weight, and the selectivity coefficient of p-isobutylstyrene was 83.3%.

EXPERIMENTAL EXAMPLE 65

Preparation of Methyl α-(4-isobutylphenyl)propionate

Hydroesterification Reaction

In a 200-ml autoclave equipped with a stirrer were placed 25.0 g of p-isobutylstyrene having 97.9% by weight purity obtained by distilling/purifying the organic phase of the dehydrogenated material in Experimental Example 64, 10.0 ml of methanol, 100 ml of toluene as a solvent, 0.0271 g of $PdCl_2$ as a catalyst, 0.0105 g of $CuCl_2$ as a promotor and 0.0812 g of triphenylphosphine as a ligand. The temperature in the autoclave was then elevated up to 90° C. under stirring, and reaction was performed for 8 hours, while the pressure in the autoclave was maintained at 70 kg/cm² with carbon monoxide. After the completion of the reaction, cooling followed, and the reaction mixture was then analyzed by means of a gas chromatography. As a result, the conversion of p-isobutylstyrene was 99.8%, the selectivity coefficient of methyl α-(4-isobutylphenyl)-propionate was 90.2%.

EXPERIMENTAL EXAMPLE 66

Preparation of α-(4-isobutylphenyl)propionic Acid

Hydrolysis Reaction

Fifteen grams of methyl α-(4-isobutylphenyl)propionate having 99.0% purity obtained by distilling the reaction mixture in Experimental Example 65 and 75 ml of a 10% aqueous sodium hydroxide solution were refluxed with stirring for about 3 hours in order to perform hydrolysis. After cooling, the mixture was allowed to stand, and the separated lower layer, i.e., water phase was then washed with normal hexane.

A 5% hydrochloric acid solution was added to the water phase so as to adjust its pH to 2, and the separated oil was then extracted with normal hexane and washed with water. Afterward, normal hexane was vaporized/removed under reduced pressure, and thereby obtaining 12.0 g of light yellow crude α-(4-isobutylphenyl)propionic acid crystals.

Crude α-(4-isobutylphenyl)propionic acid was then recrystallized with a normal hexane solvent in order to obtain 10.4 g of white purified α-(4-isobutylphenyl)propionic acid (melting point=75°-76° C.). Spectra and the like of this product were in accord with the standards.

COMPARATIVE EXAMPLE 1

Following the same procedure as in Experimental Example 1, 500 ml of ethylbenzene having 99.8% by weight purity was reacted with ethylene. After the completion of the reaction, the reaction mixture was analyzed by a gas chromatography. The composition of the reaction mixture is set forth in the following table.

TABLE

| | |
|---|---|
| Ethylbenzene | 71.7% by weight |
| Diethylbenzene | 22.7% by weight |
| ortho- | 6.3% by weight |
| meta- | 6.9% by weight |
| para- | 9.5% by weight |
| Triethylbenzene | 4.5% by weight |
| Others | 1.1% by weight |

As a result, the conversion of ethylbenzene was 28.2% by weight, and position isomers of diethylbenzene were present in a ratio of o:m:p=28:30:42.

COMPARATIVE EXAMPLE 2

Following the same procedure as in Experimental Example 1, 500 ml of isopropylbenzene having 100% by weight purity was reacted with ethylene. After the completion of the reaction, the reaction mixture was analyzed by a gas chromatography. The composition of the reaction mixture is set forth in the following table.

TABLE

| | |
|---|---|
| Isopropylbenzene | 65.3% by weight |
| Isoproplyethylbenzene | 15.8% by weight |
| ortho- | 1.7% by weight |
| meta- | 8.0% by weight |
| para- | 6.1% by weight |
| Isoproplydiethylbenzene | 9.5% by weight |
| Others | 9.4% by weight |

As a result, the conversion of isopropylbenzene was 34.7% by weight, and position isomers of isopropylethylbenzene were present in a ratio of o:m:p=11:51:38.

COMPARATIVE EXAMPLE 3

Following the same procedure as in Experimental Example 1, 500 ml of sec-butylbenzene having 99.8% by weight purity was reacted with ethylene. After the completion of the reaction, the reaction mixture was analyzed by a gas chromatography. The composition of the reaction mixture is set forth in the following table.

TABLE

| | |
|---|---|
| sec-Butylbenzene | 73.1% by weight |
| sec-Butylethylbenzene | 11.5% by weight |
| ortho- | 1.4% by weight |
| meta- | 5.6% by weight |
| para- | 4.5% by weight |
| sec-Butylethylbenzene | 9.9% by weight |
| Others | 5.5% by weight |

As a result, the conversion of sec-butylbenzene was 26.8% by weight, and position isomers of sec-butylethylbenzene were present in a ratio of o:m:p=12:49:39.

COMPARATIVE EXAMPLE 4

Following the same procedure as in Experimental Example 24, p-sec-butylethylbenzene (purity=97.5% by weight) was subjected to dehydrogenation reaction. The results are set forth in the following table.

TABLE

| Reaction temperature | 550° C. |
| --- | --- |
| Contact time | 0.20 second |
| Molar ratio of steam | 93 |
| Conversion of p-sec-Butylethylbenzene | 43.4% |

| Composition of Reaction Products | |
| --- | --- |
| p-sec-Butylethylbenzene | 55.4% by weight |
| p-sec-Butylstyrene | 6.5% by weight |
| p-sec-Butenylethylbenzene | 13.3% by weight |
| p-sec-Butenylstyrene | 14.6% by weight |
| unidentified | 10.2% by weight |

What is claimed is:

1. A method of preparing α-(4-isobutylphenyl) propionic acid or esters thereof which comprises
   (a) reacting isobutylbenzene with ethylene at a temperature ranging from −10° to 600° C. and at a pressure of at least 1 kg/cm² in a molar ratio of ethylene/isobutylbenzene ranging from 0.005–100 in the presence of a first acid catalyst, thereby forming p-isobutylethylbenzene;
   (b) dehydrogenating the p-isobutylethylbenzene at a temperature ranging from 300° to 650° C., and at a reaction pressure of at most 50 kg/cm² in the presence of a dehydrogenation metal catalyst containing a metal selected from the group consisting of a Group IB, IIB, VIA, VIIA and VIII metal; and
   (c) reacting the p-isobutylstyrene thus formed with carbon monoxide and water or alkyl alcohol in the presence of a transition metal complex carbonylation catalyst at a temperature ranging from 40° to 250° C. and a carbon monoxide pressure ranging from 10 to 600 Kg/cm².

2. A method of preparing α-(4-isobutylphenyl) propionic acid or alkyl esters thereof which comprises
   (a) reacting 4-ethyltoluene with propylene at a temperature ranging from 150° to 250° C. at a pressure of at least 15 kg/cm² in the presence of at least 3 milligram atom of an alkali metal per mold of 4-ethyltoluene, distilling the product and collecting the fraction containing the 4-isobutylethylbenzene and having a boiling point ranging from 190° to 220° C.;
   (b) dehydrogenating the 4-isobutylethylbenzene at a temperature ranging from 300° to 650° C., at a reaction pressure of at most 50 kg/cm² in the presence of a dehydrogenation metal catalyst containing a metal selected from the group consisting of Group IB, IIB, VI, VIIA and VIII metal; and
   (c) reacting the p-isobutylstyrene thus formed with carbon monoxide and water or alkyl alcohol in the presence of a transition metal complex carbonylation catalyst at a temperature ranging from 40° to 250° C. and a carbon monoxide pressure ranging from 10 to 600 kg/cm².

3. A method of preparing α-(4-isobutylphenyl) propionaldehyde which comprises:
   (a) reacting isobutylbenzene with ethylene at a temperature ranging from −10° to 600° C. at a pressure of at least 1 kg/cm² in a molar ratio of ethylene/isobutylbenzene ranging from 0.005 to 100 in the presence of a first acid catalyst, thereby forming p-isobutylethylbenzene;
   (b) dehydrogenating the p-isobutylethylbenzene at a temperature ranging from 300° to 650° C. and at a pressure of at most 50 kg/cm² in the presence of a dehydrogenation metal catalyst containing a metal selected from the group consisting of Group IB, IIB, VIA, VIIA and VIII metal; and
   (c) reacting the p-isobutylstyrene thus formed with carbon monoxide and hydrogen in the presence of a transition metal complex carbonylation catalyst at a temperature ranging from 40° to 150° C. and a mixed pressure of carbon monoxide and hydrogen ranging from 10 to 600 kg/cm².

4. A method of preparing α-(4-isobutylphenyl) propionaldehyde which comprises
   reacting 4-ethyltoluene with propylene at a temperature ranging from 150° to 250° C. at a pressure of at least 15 kg/cm² in the presence of at least 3 milligram atom of an alkali metal per mole of 4-ethyltoluene, distilling the product and collecting the fraction containing the 4-isobutylbenzene having a boiling point ranging from 190° to 220° C.;
   (b) dehydrogenating the p-isobutylethylbenzene thus formed at a temperature ranging from 300° to 650° C. at a pressure of at most 50 kg/cm² in the presence of a dehydrogenation metal catalyst containing a metal selected from the group consisting of a Group IB, IIB, VIA, and VIII metal; and
   (c) reacting the p-isobutylstyrene thus formed with carbon monoxide and hydrogen in the presence of a transition metal complex carbonylation catalyst at a temperature ranging from 40° to 150° C. and a mixed pressure of carbon monoxide and hydrogen ranging from 10 to 600 kg/cm².

5. A method of preparing α-(4-isobutylphenyl) propionic acid by oxidizing the α-(4-isobutylphenyl) propionaldehyde that is formed according to claims 3 or 4.

6. A method of preparing α-(4-isobutylphenyl) propionic acid which comprises hydrolyzing the alkyl ester of α-(4-isobutylphenyl) propionic acid that is formed according to claims 1 or 2.

7. A method as in one of claims 1–4 wherein the dehydrogenation occurs with a contact time of 0.005 to 20 seconds.

8. A method as in either claims 1 or 3 wherein the molar ratio of ethylene/isobutylbenzene ranges from 0.01 to 50.

9. The method as in either claim 1 or 3 wherein o-isobutylethylbenzene, m-isobutylethylbenzene, isobutylpolyethylbenzene or mixtures thereof are additionally formed in Step (a).

10. The method according to claim 9 wherein the o-isobutylethylbenzene, m-isobutylethylbenzene, the isobutylpolyethylbenzene or a mixture thereof undergoes disproportionation at a reaction temperature of −10° to 600° C. to form p-isobutylethylbenzene.

11. The method according to claim 10 wherein a second acid catalyst is additionally present.

12. The method as in claims 1 or 3 wherein the first acid catalyst is selected from the group consisting of solid acids, protonic inorganic acids, protonic organic acids, heteropoly acids, isopoly acids and strong acid type cation exchange resins.

13. The method as in claims 1 or 3 wherein said acid catalyst is silica alumina and said reaction temperature ranges from 150° to 600° C.

14. The method as in claims 1 or 3 wherein said acid catalyst is trifluoromethanesulfonic acid and said reaction temperature ranges from −10° to 200° C.

15. The method as in claims 1 or 3 wherein said first acid catalyst is hydrogen fluoride and the reaction temperature ranges from −10° to 200° C.

16. The method as in claims 1 or 3 wherein said first acid catalyst is a heteropoly acid and the reaction temperature ranges from 150° to 600° C.

17. The method as in claims 1 or 3 wherein said first acid catalyst is HX type zeolite, HY type zeolite or hydrogen faujasite and the reaction temperature ranges from 100° to 400° C.

18. The method according to claim 11 wherein said second acid catalyst is selected from the group consisting of solid acids, protonic inorganic acids, protonic organic acids, heteropoly acids, isopoly acids and strong acid type cation exchange resins.

19. The method according to claim 11 wherein said second acid catalyst is silica alumina and said reaction temperature ranges from 150° to 600° C.

20. The method according to claim 11 wherein said second acid catalyst is trifluoromethanesulfonic acid and said reaction temperature ranges from −10° to 200° C.

21. The method according to claim 11 wherein said second acid catalyst is hydrogen fluoride and the reaction temperature ranges from −10° to 200° C.

22. The method according to claim 11 wherein said second acid catalyst is a heteropoly acid and the reaction temperature ranges from 150° to 600° C.

23. The method according to claim 11 wherein said second acid catalyst is HX type zeolite, HY type zeolite or hydrogen faujasite and the reaction temperature ranges from 100° to 400° C.

24. The method according to claims 2 or 4 wherein the separation is effected by feeding a mixture containing at least 5% by weight of p-isobutylethylbenzene to a distillation column having 20 or more theoretical plates, then distilling the mixture and separating and recovering the p-isobutylethylbenzene therefrom as a fraction comprising components having boiling points 213° to 216° C. at 1 atm pressure.

25. The method according to claims 2 or 4 wherein said alkali metal for said side chain alkylation step is sodium metal, potassium metal or a mixture thereof.

26. The method according to claims 2 or 4 wherein said alkali metal for said side chain alkylation step is sodium metal mixed with an inorganic compound of potassium.

27. The method as in any one of claims 1-4 wherein the metal of the dehydrogenation metal catalyst is a metal selected from the group consisting of iron, copper, zinc, nickel, palladium, platinum, cobalt, rhodium, iridium, ruthenium, chrominum and molybdenum.

28. The method according to claim 27 wherein said dehydrogenation metal catalyst is an iron oxide catalyst or a copper chromium catalyst.

29. The method as in any one of claims 1-4 wherein said transition metal complex catalyst is a complex of a metal selected from the group consisting of palladium, rhodium, iridium, and ruthenium.

30. A method for preparing α-(4-isobutylphenyl) propionic acid or alkyl esters thereof comprising (a) dehydrogenating p-isobutylethylbenzene in a gaseous phase in the presence of dehydrogenation metal catalyst containing at least one metal selected from the group consisting of the group IB, IIB, VIA, VIIA and VIII metal at a reaction temperature ranging from 300° to 650° C., and at a reaction pressure of at most 50 kg/cm$^2$, thereby forming p-isobutylstyrene; and (b) reacting the p-isobutylstyrene with carbon monoxide and water or lower alcohol at a temperature ranging from 40° to 250° C. under a carbon monoxide partial pressure of at least 10 kg/cm$^2$ in the presence of an effective amount of a transition metal complex carbonylation catalyst.

31. A method for preparing α-(4-isobutylphenyl) propionaldehyde which comprises:

(a) dehydrogenating p-isobutylethylbenzene in a gaseous phase in the presence of an effective amount of a dehydrogenation metal catalyst containing at least one metal selected from the group consisting of the group IB, IIB, VIA, VIIA and VIII metal at a reaction temperature ranging from 300° to 650° C., at a reaction pressure of at most 50 kg/cm$^2$, thereby forming p-isobutylstyrene; and (b) reacting said isobutylstyrene with effective amounts of carbon monoxide and hydrogen at a reaction temperature ranging from 45° to 150° C. under an effective carbon monoxide partial pressure of at least 10 kg/cm$^2$ in the presence of an effective amount of a transition metal complex carbonylation catalyst.

32. The method as in claim 30 or 31 wherein the contact time in the dehydrogenation step ranges from 0.005 to 20 seconds and the p-isobutylethylbenzene conversion is at most 80% by weight.

33. The method as in claims 30 or 31 wherein said dehydrogenation metal catalyst contains at least one metal selected from the group consisting of iron, copper, zinc, nickel, palladium, platinum, cobalt, rhodium, iridium, ruthenium, chromium and molybdenum.

34. The method according to claim 33 wherein said dehydrogenation metal catalyst is an iron oxide catalyst or a copper chromium catalyst.

35. The method according to claim 31 wherein said transition metal complex carbonylation catalyst contains a transition metal selected from the group consisting of palladium, rhodium, iridium and ruthenium.

36. The method according to claim 30 wherein said transition metal carbonylation catalyst contains a transition metal selected from the group consisting of palladium, rhodium and iridium.

37. A method of preparing α-(4-isobutylphenyl) propionic acid which comprises oxidizing the α-(4-isobutylphenyl) propionaldehyde prepared in accordance with claim 31.

38. A method of preparing α-(4-isobutylphenyl) propionic acid which comprises hydrolyzing in the presence of an acid or alkali catalyst, the alkyl ester of α-(4-isobutylphenyl) propionic acid prepared in accordance with claim 30.

* * * * *

UNITED STATES PATENT AND TRADEMARK OFFICE
CERTIFICATE OF CORRECTION

PATENT NO. : 5,097,061

DATED : March 17, 1992

INVENTOR(S) : Isoo Shimizu, et al.

It is certified that error appears in the above-identified patent and that said Letters Patent is hereby corrected as shown below:

Column 1, line 25: "from" should read as --form--

Column 1, line 67: "a-" should read as -- $\alpha$ - --

Column 2, line 43: "is expensive" should read as --is also expensive--

Column 2, line 45: "proceeds intricate" should read as --proceeds via intricate--

Column 2, line 46: "that known" should read as --that the known--

Column 5, line 66: "o,," should read as --o-,--

Column 12, line 42: after "method" insert --for preparing--

Column 13, line 35: "120°60 to" should read as --120 to--

Column 13, line 45: "WHen" should read as --When--

UNITED STATES PATENT AND TRADEMARK OFFICE
CERTIFICATE OF CORRECTION

PATENT NO. : 5,097,061

DATED : March 17, 1992

INVENTOR(S) : Isoo Shimizu, et al.

It is certified that error appears in the above-identified patent and that said Letters Patent is hereby corrected as shown below:

Column 43, line 3:  after "under" insert --a hydrogen pressure--

Column 47, line 42, Claim 2:  "mold" should read as --mole--

Column 48, line 13, Claim 4:  before "reacting" insert --(a)--

Signed and Sealed this

Twenty-fifth Day of January, 1994

Attest:

BRUCE LEHMAN

*Attesting Officer*      *Commissioner of Patents and Trademarks*